United States Patent
Brown

(10) Patent No.: US 8,005,690 B2
(45) Date of Patent: Aug. 23, 2011

(54) DYNAMIC MODELING AND SCORING RISK ASSESSMENT

(75) Inventor: Stephen J. Brown, Woodside, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 1049 days.

(21) Appl. No.: 11/835,593

(22) Filed: Aug. 8, 2007

(65) Prior Publication Data

US 2008/0046268 A1  Feb. 21, 2008

Related U.S. Application Data

(63) Continuation of application No. 09/625,080, filed on Jul. 25, 2000, now Pat. No. 7,305,348, which is a continuation of application No. 09/160,970, filed on Sep. 25, 1998, now Pat. No. 6,240,393.

(51) Int. Cl.
*G06Q 10/00* (2006.01)
*G06F 19/00* (2011.01)

(52) U.S. Cl. ............................................. 705/2; 705/3

(58) Field of Classification Search ................... 705/2–3
See application file for complete search history.

(56) References Cited

U.S. PATENT DOCUMENTS

| | | |
|---|---|---|
| 3,426,150 A | 2/1969 | Tygart |
| 3,566,365 A | 2/1971 | Rawson et al. |
| 3,566,370 A | 2/1971 | Worthington, Jr. et al. |
| 3,581,072 A | 5/1971 | Nymeyer |
| 3,768,014 A | 10/1973 | Smith |

(Continued)

FOREIGN PATENT DOCUMENTS

EP  0286456  10/1988

(Continued)

OTHER PUBLICATIONS

"The 'Wellness' Discount Plans", Glenn Kramon, New York Times, Sep. 22, 1987, p. D2.*

(Continued)

*Primary Examiner* — Luke Gilligan
*Assistant Examiner* — Joseph Burgess
(74) *Attorney, Agent, or Firm* — Suiter Swantz pc llo

(57) ABSTRACT

The invention provides for modeling and scoring risk-assessment and a set of insurance products derived therefrom. Risk indicators are determined at a selected time. A population is assessed at that time and afterward for those risk indicators and for consequences associated therewith. Population members are coupled to client devices for determining risk indicators and consequences. A server receives data from each client, and in response thereto and in conjunction with an expert operator, (1) reassesses weights assigned to the risk indicators, (2) determines new risk indicators, (3) determines new measures for determining risk indicators and consequences, and (4) presents treatment options to each population member. The server determines, in response to the data from each client, and possibly other data, a measure of risk for each indicated consequence or for a set of such consequences. The server provides this measure with regard to each population member, or with regard to population subsets. The expert operator uses this measure to determine either (1) an individual course of treatment, (2) a resource utilization review model, (3) a risk-assessment model, or (4) an insurance pricing model, for each individual population member or for selected population subsets. Information requested by the client, information determined and presented by the server, and responsive measurements, are adapted dynamically to changing population aspects or changing population membership, or of an external environment having relevance to the population.

10 Claims, 13 Drawing Sheets

U.S. PATENT DOCUMENTS

| | | |
|---|---|---|
| 3,811,116 A | 5/1974 | Takeuchi et al. |
| 3,883,235 A | 5/1975 | Lynn et al. |
| 3,910,257 A | 10/1975 | Fletcher et al. |
| 3,920,005 A | 11/1975 | Gombrich et al. |
| 3,996,928 A | 12/1976 | Marx |
| 4,004,577 A | 1/1977 | Sarnoff |
| 4,051,522 A | 9/1977 | Healy et al. |
| 4,060,915 A | 12/1977 | Conway |
| 4,130,881 A | 12/1978 | Haessler et al. |
| 4,150,284 A | 4/1979 | Trenkler et al. |
| 4,151,407 A | 4/1979 | McBride et al. |
| 4,151,831 A | 5/1979 | Lester |
| 4,173,971 A | 11/1979 | Karz |
| 4,216,462 A | 8/1980 | McGrath et al. |
| 4,227,526 A | 10/1980 | Goss |
| 4,253,521 A | 3/1981 | Savage |
| 4,259,548 A | 3/1981 | Fahey et al. |
| 4,270,547 A | 6/1981 | Steffen et al. |
| 4,296,756 A | 10/1981 | Dunning et al. |
| 4,347,568 A | 8/1982 | Giguere et al. |
| 4,347,851 A | 9/1982 | Jundanian |
| 4,360,345 A | 11/1982 | Hon |
| 4,412,287 A | 10/1983 | Braddock, III |
| 4,417,306 A | 11/1983 | Citron et al. |
| 4,422,081 A | 12/1983 | Woods |
| 4,428,733 A | 1/1984 | Kumar-Misir |
| 4,449,536 A | 5/1984 | Weaver |
| 4,465,077 A | 8/1984 | Schneider |
| 4,473,884 A | 9/1984 | Behl |
| 4,518,361 A | 5/1985 | Conway |
| 4,519,398 A | 5/1985 | Lisiecki et al. |
| 4,531,527 A | 7/1985 | Reinhold, Jr. |
| 4,546,436 A | 10/1985 | Schneider et al. |
| 4,566,461 A | 1/1986 | Lubell et al. |
| 4,576,578 A | 3/1986 | Parker et al. |
| 4,592,546 A | 6/1986 | Fascenda et al. |
| 4,627,445 A | 12/1986 | Garcia |
| 4,674,652 A | 6/1987 | Aten et al. |
| 4,686,624 A | 8/1987 | Blum et al. |
| 4,694,490 A | 9/1987 | Harvey et al. |
| 4,695,954 A | 9/1987 | Rose et al. |
| 4,712,562 A | 12/1987 | Ohayon et al. |
| 4,722,349 A | 2/1988 | Baumberg |
| 4,729,381 A | 3/1988 | Harada et al. |
| 4,730,253 A | 3/1988 | Gordon |
| 4,731,726 A | 3/1988 | Allen, III |
| 4,738,451 A | 4/1988 | Logg |
| 4,768,229 A | 8/1988 | Benjamin et al. |
| 4,779,199 A | 10/1988 | Yoneda et al. |
| 4,782,511 A | 11/1988 | Nemec et al. |
| 4,789,928 A | 12/1988 | Fujisaki |
| 4,796,639 A | 1/1989 | Snow et al. |
| 4,799,156 A | 1/1989 | Shavit et al. |
| 4,799,199 A | 1/1989 | Scales, III et al. |
| 4,803,625 A | 2/1989 | Fu et al. |
| 4,835,372 A | 5/1989 | Gombrich et al. |
| 4,838,275 A | 6/1989 | Lee |
| 4,846,797 A | 7/1989 | Howson et al. |
| 4,853,521 A | 8/1989 | Claeys et al. |
| 4,858,354 A | 8/1989 | Gettler |
| 4,858,617 A | 8/1989 | Sanders |
| 4,890,621 A | 1/1990 | Hakky |
| 4,894,777 A | 1/1990 | Negishi et al. |
| 4,897,869 A | 1/1990 | Takahashi |
| 4,899,839 A | 2/1990 | Dessertine et al. |
| 4,903,201 A | 2/1990 | Wagner |
| 4,907,973 A | 3/1990 | Hon |
| 4,931,934 A | 6/1990 | Snyder |
| 4,933,873 A | 6/1990 | Kaufman et al. |
| 4,933,876 A | 6/1990 | Markoff et al. |
| 4,950,246 A | 8/1990 | Muller |
| 4,950,264 A | 8/1990 | Osborn, III |
| 4,953,552 A | 9/1990 | DeMarzo |
| 4,958,632 A | 9/1990 | Duggan |
| 4,958,641 A | 9/1990 | Digby et al. |
| 4,967,756 A | 11/1990 | Hewitt |
| 4,977,899 A | 12/1990 | Digby et al. |
| 4,978,303 A | 12/1990 | Lampbell |
| 4,978,335 A | 12/1990 | Arthur, III |
| 4,979,509 A | 12/1990 | Hakky |
| 5,007,429 A | 4/1991 | Treatch et al. |
| 5,009,645 A | 4/1991 | Silver et al. |
| 5,016,172 A | 5/1991 | Dessertine |
| 5,019,974 A | 5/1991 | Beckers |
| 5,024,225 A | 6/1991 | Fang |
| 5,025,374 A | 6/1991 | Roizen et al. |
| 5,034,807 A | 7/1991 | Von Kohorn |
| 5,035,625 A | 7/1991 | Munson et al. |
| 5,036,462 A | 7/1991 | Kaufman et al. |
| 5,049,487 A | 9/1991 | Phillips et al. |
| 5,050,612 A | 9/1991 | Matsumura |
| 5,056,059 A | 10/1991 | Tivig et al. |
| 5,059,394 A | 10/1991 | Phillips et al. |
| 5,065,315 A | 11/1991 | Garcia |
| 5,068,536 A | 11/1991 | Rosenthal |
| 5,074,317 A | 12/1991 | Bondell et al. |
| 5,077,476 A | 12/1991 | Rosenthal |
| 5,077,665 A | 12/1991 | Silverman et al. |
| 5,095,798 A | 3/1992 | Okada et al. |
| 5,104,380 A | 4/1992 | Holman et al. |
| 5,109,414 A | 4/1992 | Harvey et al. |
| 5,109,974 A | 5/1992 | Beer et al. |
| 5,111,396 A | 5/1992 | Mills et al. |
| 5,111,817 A | 5/1992 | Clark et al. |
| 5,111,818 A | 5/1992 | Suzuki et al. |
| 5,120,230 A | 6/1992 | Clark et al. |
| 5,120,421 A | 6/1992 | Glass et al. |
| 5,128,752 A | 7/1992 | Von Kohorn |
| 5,134,391 A | 7/1992 | Okada |
| 5,142,358 A | 8/1992 | Jason |
| 5,142,484 A | 8/1992 | Kaufman et al. |
| 5,143,378 A | 9/1992 | Joel |
| 5,171,977 A | 12/1992 | Morrison |
| 5,176,502 A | 1/1993 | Sanderson et al. |
| 5,182,707 A | 1/1993 | Cooper et al. |
| 5,204,670 A | 4/1993 | Stinton |
| 5,219,322 A | 6/1993 | Weathers |
| 5,222,020 A | 6/1993 | Takeda |
| 5,226,895 A | 7/1993 | Harris |
| 5,227,874 A | 7/1993 | Von Kohorn |
| 5,228,450 A | 7/1993 | Sellers |
| 5,230,629 A | 7/1993 | Buschke |
| 5,231,990 A | 8/1993 | Gauglitz |
| 5,243,515 A | 9/1993 | Lee |
| 5,249,044 A | 9/1993 | Von Kohorn |
| 5,251,126 A | 10/1993 | Kahn et al. |
| 5,261,401 A | 11/1993 | Baker et al. |
| 5,262,943 A | 11/1993 | Thibado et al. |
| 5,265,888 A | 11/1993 | Yamamoto et al. |
| 5,266,179 A | 11/1993 | Nankai et al. |
| 5,275,159 A | 1/1994 | Griebel |
| 5,282,950 A | 2/1994 | Dietze et al. |
| 5,295,491 A | 3/1994 | Gevins |
| 5,299,121 A | 3/1994 | Brill et al. |
| 5,301,105 A | 4/1994 | Cummings, Jr. |
| 5,304,112 A | 4/1994 | Mrklas et al. |
| 5,304,468 A | 4/1994 | Phillips et al. |
| 5,307,263 A | 4/1994 | Brown |
| 5,309,919 A | 5/1994 | Snell et al. |
| 5,321,009 A | 6/1994 | Baeder et al. |
| 5,325,288 A | 6/1994 | Satou |
| 5,329,459 A | 7/1994 | Kaufman et al. |
| 5,329,608 A | 7/1994 | Bocchieri et al. |
| 5,331,549 A | 7/1994 | Crawford, Jr. |
| 5,333,981 A | 8/1994 | Pronovost et al. |
| 5,335,338 A | 8/1994 | Proesel |
| 5,339,821 A | 8/1994 | Fujimoto |
| 5,341,291 A | 8/1994 | Roizen et al. |
| 5,343,239 A | 8/1994 | Lappington et al. |
| 5,344,324 A | 9/1994 | O'Donnell et al. |
| 5,357,427 A | 10/1994 | Langen et al. |
| 5,366,896 A | 11/1994 | Margrey et al. |
| 5,368,562 A | 11/1994 | Blomquist et al. |
| 5,371,687 A | 12/1994 | Holmes, II et al. |
| 5,375,604 A | 12/1994 | Kelly et al. |
| 5,377,100 A | 12/1994 | Pope et al. |
| 5,390,238 A | 2/1995 | Kirk et al. |

| | | |
|---|---|---|
| 5,399,821 A | 3/1995 | Inagaki et al. |
| 5,410,471 A | 4/1995 | Alyfuku et al. |
| 5,410,474 A | 4/1995 | Fox |
| 5,429,140 A | 7/1995 | Burdea et al. |
| 5,431,690 A | 7/1995 | Schaldach et al. |
| 5,431,691 A | 7/1995 | Snell et al. |
| 5,434,611 A | 7/1995 | Tamura |
| 5,438,607 A | 8/1995 | Przygoda, Jr. et al. |
| 5,438,983 A | 8/1995 | Falcon |
| 5,441,047 A | 8/1995 | David et al. |
| 5,449,334 A | 9/1995 | Kingsbury |
| 5,454,721 A | 10/1995 | Kuch |
| 5,454,722 A | 10/1995 | Holland et al. |
| 5,456,606 A | 10/1995 | McIntyre |
| 5,456,692 A | 10/1995 | Smith, Jr. et al. |
| 5,458,123 A | 10/1995 | Unger |
| 5,467,269 A | 11/1995 | Flaten |
| 5,471,039 A | 11/1995 | Irwin, Jr. et al. |
| 5,471,382 A | 11/1995 | Tallman et al. |
| 5,483,276 A | 1/1996 | Brooks et al. |
| 5,488,412 A | 1/1996 | Majeti et al. |
| 5,488,423 A | 1/1996 | Walkingshaw et al. |
| 5,501,231 A | 3/1996 | Kaish |
| 5,502,636 A | 3/1996 | Clarke |
| 5,502,726 A | 3/1996 | Fischer |
| 5,504,519 A | 4/1996 | Remillard |
| 5,517,405 A | 5/1996 | McAndrew et al. |
| 5,518,001 A | 5/1996 | Snell |
| 5,519,058 A | 5/1996 | Gonick et al. |
| 5,519,433 A | 5/1996 | Lappington et al. |
| 5,523,232 A | 6/1996 | Sechler |
| 5,536,249 A | 7/1996 | Castellano et al. |
| 5,542,420 A | 8/1996 | Goldman et al. |
| 5,544,649 A | 8/1996 | David et al. |
| 5,546,943 A | 8/1996 | Gould |
| 5,549,117 A | 8/1996 | Tacklind et al. |
| 5,550,575 A | 8/1996 | West et al. |
| 5,553,609 A | 9/1996 | Chen et al. |
| 5,558,638 A | 9/1996 | Evers et al. |
| 5,564,429 A | 10/1996 | Bornn et al. |
| 5,569,212 A | 10/1996 | Brown |
| 5,572,421 A | 11/1996 | Altman et al. |
| 5,572,646 A | 11/1996 | Kawai et al. |
| 5,574,828 A | 11/1996 | Hayward et al. |
| 5,576,952 A | 11/1996 | Stutman et al. |
| 5,583,758 A | 12/1996 | McIlroy et al. |
| 5,590,648 A | 1/1997 | Mitchell et al. |
| 5,593,349 A | 1/1997 | Miguel et al. |
| 5,593,390 A | 1/1997 | Castellano et al. |
| 5,594,637 A | 1/1997 | Eisenberg et al. |
| 5,596,994 A | 1/1997 | Bro |
| 5,597,307 A | 1/1997 | Redford et al. |
| 5,601,435 A | 2/1997 | Quy |
| 5,613,495 A | 3/1997 | Mills et al. |
| 5,619,991 A | 4/1997 | Sloane |
| 5,624,265 A | 4/1997 | Redford et al. |
| 5,628,309 A | 5/1997 | Brown |
| 5,629,981 A | 5/1997 | Nerlikar |
| 5,631,844 A | 5/1997 | Margrey et al. |
| 5,633,910 A | 5/1997 | Cohen |
| 5,635,532 A | 6/1997 | Samid |
| 5,639,471 A | 6/1997 | Chait et al. |
| 5,640,569 A | 6/1997 | Miller et al. |
| 5,640,953 A | 6/1997 | Bishop et al. |
| 5,642,731 A | 7/1997 | Kehr |
| 5,642,936 A | 7/1997 | Evans |
| 5,651,363 A | 7/1997 | Kaufman et al. |
| 5,651,775 A | 7/1997 | Walker et al. |
| 5,659,691 A | 8/1997 | Durward et al. |
| 5,666,487 A | 9/1997 | Goodman et al. |
| 5,670,711 A | 9/1997 | Detournay et al. |
| 5,675,635 A | 10/1997 | Vos et al. |
| 5,678,562 A | 10/1997 | Sellers |
| 5,678,571 A | 10/1997 | Brown |
| 5,679,075 A | 10/1997 | Forrest et al. |
| 5,680,590 A | 10/1997 | Parti |
| 5,680,866 A | 10/1997 | Kangas et al. |
| 5,687,322 A | 11/1997 | Deaton et al. |
| 5,687,717 A | 11/1997 | Halpern et al. |
| 5,687,734 A | 11/1997 | Dempsey et al. |
| 5,689,652 A | 11/1997 | Lupien et al. |
| 5,692,906 A | 12/1997 | Corder |
| 5,704,364 A | 1/1998 | Saltzstein et al. |
| 5,704,366 A | 1/1998 | Tacklind et al. |
| 5,704,902 A | 1/1998 | Vandenbelt et al. |
| 5,704,922 A | 1/1998 | Brown |
| 5,710,178 A | 1/1998 | Samid |
| 5,710,918 A | 1/1998 | Lagarde et al. |
| 5,711,297 A | 1/1998 | Iliff |
| 5,714,319 A | 2/1998 | Joutel et al. |
| 5,715,451 A | 2/1998 | Marlin |
| 5,715,823 A | 2/1998 | Wood et al. |
| 5,717,739 A | 2/1998 | Dyer et al. |
| 5,717,913 A | 2/1998 | Driscoll |
| 5,720,733 A | 2/1998 | Brown |
| 5,722,418 A * | 3/1998 | Bro ............................. 600/545 |
| 5,727,153 A | 3/1998 | Powell |
| 5,730,124 A | 3/1998 | Yamauchi |
| 5,730,654 A | 3/1998 | Brown |
| 5,732,696 A | 3/1998 | Rapoport et al. |
| 5,732,709 A | 3/1998 | Tacklind et al. |
| 5,734,413 A | 3/1998 | Lappington et al. |
| 5,749,083 A | 5/1998 | Koda et al. |
| 5,752,234 A | 5/1998 | Withers |
| 5,754,740 A | 5/1998 | Fukuoka et al. |
| 5,760,771 A | 6/1998 | Blonder et al. |
| 5,772,585 A | 6/1998 | Lavin et al. |
| 5,778,882 A | 7/1998 | Raymond et al. |
| 5,782,814 A | 7/1998 | Brown et al. |
| 5,785,650 A | 7/1998 | Akasaka et al. |
| 5,787,295 A | 7/1998 | Nakao |
| 5,791,342 A | 8/1998 | Woodard |
| 5,792,117 A | 8/1998 | Brown |
| 5,793,969 A | 8/1998 | Kamentsky et al. |
| 5,794,219 A | 8/1998 | Brown |
| 5,794,251 A | 8/1998 | Watanabe et al. |
| 5,796,393 A | 8/1998 | MacNaughton et al. |
| 5,799,318 A | 8/1998 | Cardinal et al. |
| 5,800,458 A | 9/1998 | Wingrove |
| 5,802,494 A | 9/1998 | Kuno |
| 5,802,534 A | 9/1998 | Hatayama et al. |
| 5,806,057 A | 9/1998 | Gormley et al. |
| 5,807,336 A | 9/1998 | Russo et al. |
| 5,810,747 A | 9/1998 | Brudny et al. |
| 5,819,735 A | 10/1998 | Mansfield et al. |
| 5,822,544 A | 10/1998 | Chaco et al. |
| 5,822,715 A | 10/1998 | Worthington et al. |
| 5,825,283 A | 10/1998 | Camhi |
| 5,827,180 A | 10/1998 | Goodman |
| 5,828,943 A | 10/1998 | Brown |
| 5,832,448 A | 11/1998 | Brown |
| 5,835,896 A | 11/1998 | Fisher et al. |
| 5,840,020 A | 11/1998 | Heinonen et al. |
| 5,842,976 A | 12/1998 | Williamson |
| 5,868,669 A | 2/1999 | Iliff |
| 5,868,683 A | 2/1999 | Protopapas et al. |
| 5,875,432 A | 2/1999 | Sehr |
| 5,879,163 A | 3/1999 | Brown et al. |
| 5,882,338 A | 3/1999 | Gray |
| 5,887,133 A | 3/1999 | Brown et al. |
| 5,893,077 A | 4/1999 | Griffin |
| 5,893,098 A | 4/1999 | Peters et al. |
| 5,897,493 A | 4/1999 | Brown |
| 5,899,855 A | 5/1999 | Brown |
| 5,911,687 A | 6/1999 | Sato et al. |
| 5,913,310 A | 6/1999 | Brown |
| 5,913,826 A | 6/1999 | Blank |
| 5,918,603 A | 7/1999 | Brown |
| 5,920,477 A | 7/1999 | Hofberg et al. |
| 5,933,136 A | 8/1999 | Brown |
| 5,935,060 A | 8/1999 | Iliff |
| 5,937,387 A * | 8/1999 | Summerell et al. ................ 705/2 |
| 5,940,801 A | 8/1999 | Brown |
| 5,940,802 A | 8/1999 | Hildebrand et al. |
| 5,941,829 A | 8/1999 | Saltzstein et al. |
| 5,945,651 A | 8/1999 | Chorosinski et al. |
| 5,951,300 A | 9/1999 | Brown |
| 5,954,641 A | 9/1999 | Kehr et al. |

| | | |
|---|---|---|
| 5,956,501 A | 9/1999 | Brown |
| 5,960,403 A | 9/1999 | Brown |
| 5,961,446 A | 10/1999 | Beller et al. |
| 5,966,526 A | 10/1999 | Yokoi |
| 5,971,855 A | 10/1999 | Ng |
| 5,971,922 A | 10/1999 | Arita et al. |
| 5,983,003 A | 11/1999 | Lection et al. |
| 5,983,217 A | 11/1999 | Khosravi-Sichani et al. |
| 5,987,471 A | 11/1999 | Bodine et al. |
| 5,995,969 A | 11/1999 | Lee et al. |
| 5,997,476 A | 12/1999 | Brown |
| 5,997,502 A | 12/1999 | Reilly et al. |
| 6,001,065 A | 12/1999 | DeVito |
| 6,022,315 A | 2/2000 | Iliff |
| 6,022,615 A | 2/2000 | Rettenbacher |
| 6,023,686 A | 2/2000 | Brown |
| 6,024,281 A | 2/2000 | Shepley |
| 6,024,699 A * | 2/2000 | Surwit et al. ........... 600/300 |
| 6,029,138 A | 2/2000 | Khorasani et al. |
| 6,032,119 A | 2/2000 | Brown et al. |
| 6,035,328 A | 3/2000 | Soukal |
| 6,046,761 A | 4/2000 | Echerer |
| 6,049,794 A | 4/2000 | Jacobs et al. |
| 6,050,940 A | 4/2000 | Braun et al. |
| 6,055,314 A | 4/2000 | Spies et al. |
| 6,055,487 A | 4/2000 | Margery et al. |
| 6,055,506 A | 4/2000 | Frasca, Jr. |
| 6,057,758 A | 5/2000 | Dempsey et al. |
| 6,068,615 A | 5/2000 | Brown et al. |
| 6,101,478 A | 8/2000 | Brown |
| 6,110,148 A | 8/2000 | Brown et al. |
| 6,113,578 A | 9/2000 | Brown |
| 6,138,145 A | 10/2000 | Kawanaka |
| 6,144,837 A | 11/2000 | Quy |
| 6,151,586 A | 11/2000 | Brown |
| 6,161,095 A | 12/2000 | Brown |
| 6,167,362 A | 12/2000 | Brown et al. |
| 6,167,386 A | 12/2000 | Brown |
| 6,168,563 B1 | 1/2001 | Brown |
| 6,177,940 B1 | 1/2001 | Bond et al. |
| 6,186,145 B1 | 2/2001 | Brown |
| 6,189,029 B1 | 2/2001 | Fuerst |
| D439,242 S | 3/2001 | Brown et al. |
| 6,210,272 B1 | 4/2001 | Brown |
| 6,221,012 B1 | 4/2001 | Maschke et al. |
| 6,233,539 B1 | 5/2001 | Brown |
| 6,240,393 B1 | 5/2001 | Brown |
| 6,246,992 B1 | 6/2001 | Brown |
| 6,248,065 B1 | 6/2001 | Brown |
| 6,260,022 B1 | 7/2001 | Brown |
| 6,270,455 B1 | 8/2001 | Brown |
| 6,270,456 B1 | 8/2001 | Iliff |
| 6,334,778 B1 | 1/2002 | Brown |
| 6,352,523 B1 | 3/2002 | Brown et al. |
| 6,368,273 B1 | 4/2002 | Brown |
| 6,370,513 B1 | 4/2002 | Kolawa et al. |
| 6,375,469 B1 | 4/2002 | Brown |
| 6,379,301 B1 | 4/2002 | Worthington et al. |
| 6,381,577 B1 | 4/2002 | Griffin |
| 6,436,036 B1 | 8/2002 | Miller-Kovach et al. |
| 6,513,532 B2 | 2/2003 | Mault et al. |
| 2002/0019748 A1 | 2/2002 | Brown |
| 2004/0106855 A1 | 6/2004 | Brown |
| 2004/0107116 A1 | 6/2004 | Brown |
| 2004/0117207 A1 | 6/2004 | Brown |
| 2004/0117208 A1 | 6/2004 | Brown |
| 2004/0117209 A1 | 6/2004 | Brown |
| 2004/0117210 A1 | 6/2004 | Brown |

FOREIGN PATENT DOCUMENTS

| | | |
|---|---|---|
| EP | 0320749 | 6/1989 |
| EP | 370599 | 5/1990 |
| EP | 0461910 | 12/1991 |
| EP | 508912 | 10/1992 |
| EP | 526166 | 2/1993 |
| EP | 0558975 | 9/1993 |
| EP | 0653718 | 5/1995 |
| EP | 676709 | 10/1995 |
| EP | 680727 | 11/1995 |
| EP | 761160 | 3/1997 |
| EP | 08131551 | 12/1997 |
| EP | 0251520 | 1/1998 |
| GB | 2218831 | 11/1989 |
| GB | 2225637 | 6/1990 |
| JP | 54005785 | 1/1979 |
| JP | 54146633 | 11/1979 |
| JP | 62226278 | 10/1987 |
| JP | 5155024 | 6/1993 |
| JP | 5266002 | 10/1993 |
| WO | WO-8501667 | 4/1985 |
| WO | WO-90/00367 | 1/1990 |
| WO | WO-9109374 | 6/1991 |
| WO | WO-93/01489 | 1/1993 |
| WO | WO-9416774 | 8/1994 |
| WO | WO-95/09386 | 4/1995 |
| WO | WO-95/20199 | 7/1995 |
| WO | WO-9522131 | 8/1995 |
| WO | WO-9529447 | 11/1995 |
| WO | WO-96/07908 | 3/1996 |
| WO | WO-96/25877 | 8/1996 |
| WO | WO-9636923 | 11/1996 |
| WO | WO-97/08605 | 3/1997 |
| WO | WO-97/12544 | 4/1997 |
| WO | WO-9737738 | 10/1997 |
| WO | WO-98/16895 | 4/1998 |

OTHER PUBLICATIONS

"Being Fit Truly May Be a Bonus", Kim Gilmore, St Petersburg Times, Apr. 3, 1997, p. 1.*
+5V Powered Isolated RS-232 Drivers/Receivers Maxim Integrated Products.
Adilman; "Videogames: Knowing the Score"; Creative Computing; v9; p. 224(5); Dec. 1983; Dialog: File 148, Acc# 01891055.
AdOptimizer—Ad Management Software for Websites, Newsbytes, pNEW10040041, Oct. 4, 1996.
Albisser, A.M. "Intelligent Instrumentation in Diabetic Management", CRC Critical Reviews in Biomedical Engineering, vol. 17, No. 1, pp. 1-24.
Anonymous, "Health Hero Network, Inc. Receives First-Ever FDA Clearance for Connecting Medical Devices to Internet", PR Newswire, (Dec. 2, 1993), 3 pages.
Antique Collector , Putting the Lot on the Net, vol. 66, Issue 9, p. 26, Downloaded from Corporate Resource Net, Nov./Dec. 1995.
Bai, "Design of home healthcare network", IEEE 1997 pp. 1657-1658.
Billiard, A., et al. "Telematic Transmission of Computerized Blood Glucose Profiles for IDDm Patients", Diabetes Care, (Feb. 1991), vol. 14, No. 2, pp. 130-134.
Blood Glucose Monitors, Portable Health Device, (1998), vol. 17(9), pp. 253-271.
Bower, "Brain Clues to Energy-efficient Learning", Science News, (Apr. 1992), v. 141; p215(1); Dialog: File 647, Acct# 12123949.
Brenman et al.; "Interaction of Nitric Oxide Synthase with the Postsynaptic Density Protein PSD-95 and α1-Syntrophin Mediated by PDZ Domaine"; Cell; vol. 84, pp. 757-767, Mar. 8, 1996; Ref: XP-002104701.
Bruce, "Health Hero Network CEO, CNNfn", Digital Jam, (Dec. 1, 1999), 3.
Bruce, et al., "The Effects of Sympathetic Nervous System Activation and Psychological Stress . . . "; Diabetologia; 35(9); 1992; 835-843; Dialog: File 5, Acc#9629427. (9 pages).
Brunetti, P., et al., "A Simulation Study on a Self-Turning Portable Controller of Blood Glucose", The International Journal of Artificial Organs, (1993), vol. 16, No. 16, pp. 51-57.
Caprihan, A., et al., "A Simple Microcomputer for Biomedical Signal Processing", IECI '78 Annual Conference Proceedings on Industrial Applications of Microprocessors, (Mar. 20, 1978), 18-23.
Cathay Pacific Airways-USA receives more than 1,300 bids during first five days of CyberAuction; Business Wire, Oct. 18, 1995, p10181119.
Cathay Pacific Airways-USA to Hold First-Ever Internet CyberAuction; CyberTravelers Can Bid for 50 Business Class Round Trips to Hong Kong—No Minimum Bid; Business Wire; p9261084; Sep. 26, 1995; Dialog: File 148, Acc#08167091.

CD-ROM Mavericks: Proprietary TV-Based Players, Byte Guide to CD-ROM, pp. 100-105.

Central Fetal Monitoring Systems with Optical Disk Storage, New Technology Brief, (Nov./Dec. 1998), vol. 2, No. 6, pp. 249-251.

Cheng, Joe H., "PCT Search Report", (Jan. 11, 1996).

DigiPet Instruction Manual, 1997.

Digital Doggie; retrieved from URL http://www.virtualpet.com/vp/farm/gigapet/ddoggie.htm Apr. 23, 2000.

Douglas, A.S., et al., "Hand-Held Glucose Monitor and Recorder", Proceedings of the Annual International Conference of the IEEE Engineering in Medicine and Biology Society, New Orleans, LA, (Nov. 1988), pp. 747-748.

Edelson; "Fashion Reevaluates Flickering Fortunes of TV Home Shopping"; WWD; v170 n87; p1(3); Nov. 8, 1995; Dialog: File 148, Acc#08289119.

EP European Search Report, From 6858P005EP, (Mar. 27, 1998).

Fabietti, P.G., et al., "Wearable System for Acquisition, Processing and Storage of the Signal from Amperometric Glucose Sensors", The International Journal of Artificial Organs, (1991), vol. 14, No. 3, pp. 175-178.

Finston, "Parent + Teacher = Healthy Child", Diabetes Forecast, (Apr. 1994), v47 n9; P26(5); Dialog: file 149, Acc# 15804228.

Fox, "Not My Type: Type B Behavior, Type I Diabetes Plus Stress Equals Blood Sugar Blues", Health, (Mar. 1998), v20 n3; pp22(1); Dialog: File 149, Acc# 06397959.

Franklin; "Proposed Auction Rules for PCS: The FCC Plans to Use Competitive Bidding, but Exact Procedures are Undefined"; Cellular Business; v10 n13; p. 18(2); Dec. 1993; Dialog: File 148, Acc#06787310.

Frieberger, Paul, "Video Game Takes on Diabetes Superhero 'Captain Novolin' Offers Treatment Tips", San Francisco Examiner, (Jun. 26, 1992), Fourth Edition, Business Section B1.

Furnham, et al; "Measuring Locus of Control: a Critique of General Children's Health- and Work-related Locus of Control Questionnaires"; British Journal of Psychology; v84 n4; p. 443(37); Nov. 1993; Dialog: File 88, Acc# 14903135.

Future of the Virtual Pet Industry, 1997 [retrieved on Apr. 23, 2000], Retrieved from <URL:www.virtualpet.com/vp/ future/future.htm>.

Gardner, et al.; "Comprehension and Appreciation of Humorous Material Following Brain Damage"; Brain; Sep. 1975; 98(3); pp. 399-412; Dialog: File 153, Acc#02859983. (14 pages).

Gauntlet (for PC) rulebook by Mindscape Inc. (Gauntlet by Apple);1985.

Giga Farm; retrieved from URL http://www.virtualpet.com/vp/farm/gigapet/gpfarm/gpfarm.htm Apr. 23, 2000.

Giga Pets, 1997 [retrieved on Apr. 23, 2000], Retrieved from <URL:www.virtualpet.com/vp/farm/gigapet/gigapet.htm>.

Gordon; "Auctions Become High Tech"; Dealer Business; v29 n7; p. 21(4); Mar. 1995; Dialog: File 148, Acc#07862519.

Guiffrida, et al., Should We Pay the Patient? Review of Financial Incentives to enhance Patient Compliance:, Biomedical Journal, (1997), vol. 315, pp. 703-707.

Hauben, Jay R., "A Brief History of the Cleveland Free-Net", available at http://www.ais.org/~irh/acn7-1.a09.html, (1995) pp. 1-4.

Hauser, et al., "Will Computers Replace or Complement the Diabetes Educator!", The Medical Journal of Australia, (Oct. 5, 1992), vol. 157, 489-491.

Horio, Hiroyuki, et al., "Clinical Telecommunication Network System for Home Monitoring", Medical & Biological Engineering & Computing, (Mar. 1994), vol. 32, 227-230.

How Flash Memory Works, Internet printout of URL address: http://www.howstuffworks.com/flash-memory4.htm, (Sep. 28, 2002), 2 pages.

Howey, et al., "A Rapidly Absorbed Analogue of Human Insulin"; Diabetes, vol. 43, Mar. 1994, pp. 396-402. (7 pages).

Hunter, "Technological Advances in Bedside Monitoring: Biosensors", Archives and Laboratory Medicine, (Jul. 1987), pp. 633-636.

Hutheesing, Nikhil, "An on-line gamble", Forbes, v157 n10 p. 288(1), May 20, 1996.

Introducing the Next Generation of About Your Diabetes, U.S. Pharmacopical Convention and American Diabetes Association, (1993).

Jaffrey et al.; "PIN: An Associated Protein Inhibitor of Neuronal Nitric Oxide Synthase"; Science; vol. 274; Nov. 1, 1996; Ref: XP 002050141.

Jimison et al., "Patient-Specific explanation in models of chronic disease", Revised Feb. 1992 Artificial Intelligence in Medicine 4 (1992) 191-205.

Jones, Chris, "Microsoft readies DocObject; technology will allow document editing in Web browsers", InfoWorld, v18 n18 p. 48(1), Apr. 29, 1996.

Kauffmann, et al., "Epidemiological Study of the Genetics and Environment of Asthma, Bronchial Hyperresponsiveness and Atrophy", Am. J. Respir. Crit. Care Med., (1997), vol. 156, pp. S123-S129.

Kaufman, Steven, B., "The Learning Game", Nation's Business, (Nov. 1993).

Kennedy et al.; "Television Computer Games: A New Look in Performance Testing"; Aviat Space Environ Med; Jan. 1982, 53(1); pp. 49-53. (5 pages); Dialog Abstract: File 155, Acc#0353751.

Kuykendall, V.G., et al., "Assessment of Self-Monitored Blood Glucose results Using a Reflectance Meter with Memory and Microcomputer", Symposium on Computer Applications in Medical Care, (Jan. 1981), vol. 70, pp. 98-102.

Lachnit, Carroll, "Hawkin's Online Auction", Photo District News, vol. 16, Issue 1, p. 18, Jan. 1996.

Lacyk, John, "PCT Search Report", (Jun. 12, 1997).

Latman, N. S., "Evaluation of Electronic, Digital Blood Glucose Monitors", Biomedical Instrumentation and Technology, (1991), vol. 25, No. 1, 43-49.

Leyerle, Beverly J., et al., "The PDMS as a Focal Point for Distributed Patient Data", International Journal of Clinical Monitoring and Computing, (1988), vol. 5, pp. 155-161.

Luebke, Cathy, "Barrett-Jackson Auction Turns High-Tech", Business Journal, vol. 16, Issue 12, pp. 11, Jan. 19, 1996.

Makikawa, M., et al., "Microprocessor-Based Memory Device for Ambulatory Heart Rate and Physical Activity Recording", Methods of Information in Medicine, (1994), vol. 33, No. 1, pp. 94-96.

Marsh, David G. "Approaches Toward the Genetic Analysis of Complex Traits Asthma and Atrophy", Am. J. Respir.Crit.Care Med., (1997), vol. 156, pp. S-133-S138.

Martinez, Fernando D., "Complexities of the Genetics of Asthma", Am.J. Respir. Crit. Care Med., (1997), vol. 156, pp. S117-S122.

Marx, Wendy, "More than just the Scores: ESPNET SportsZone is a model for expanding brand names online", InformationWeek, n576 p. 61(2), Apr. 22, 1996.

Mazzola, et al., "Video Diabetes: A Teaching Tool for Children with Insulin-Dependent Diabetes", Proceedings—7th Annual Symposium on Computer Applications in Medical Care; Washington, DC; Dialog:, (Oct. 1983), File 8, Acc# 01624462.

McCullagh, PJ et al., "Computerized paradigms for eliciting the contingent negative variation event-related potential," Proceedings of the Annual International Conference of the Engineering in Medicine & Biology Society, IEEE, Conf. 14, p2481-2483, Oct. 1992.

Meissner, et al., "Building an Integrated Clinical and Research Network", Proceedings of the SPIE, (Oct. 24, 1995), vol. 2618, p. 92-99.

Miles, Laughton E., "A Portable Microcomputer for Long-Term Physiological Monitoring in the Home and Work Environment", Medical Monitoring in the Home and Work Environment, (1990), pp. 47-57.

Mims; "Psychological Testing"; Computers & Electronics; v23; p. 22(6); Feb. 1985; Dialog: File 47, Acc# 2654858.

Moore, "New Applications Break Through Storage Boundaries", Computer Technology Review, (Oct. 1999), vol. 19, No. 10 p. 1.

MULE. rulebook by Electronic Arts, 1983.

Nano Baby Instructions; retrieved from file://C:\My Documents\Nano Baby Instructions.htm Apr. 23, 2000.

Nano Fighter Pets; retrieved from URL http://www.virtualpet.com/vp/farm/nano/nfighter.htm Apr. 23, 2000.

Nano Page, 1997 [retrieved on Apr. 23, 2000], Retrieved from <URL:www.virtualpet.com/vp/farm/nano/nano.htm>.

Octhigotchi Instruction Manual, 1997. Dino-Kun Instruction Manual, 1997.

O'Donnell; "Alan's At It Again"; Bond Buyer; v309 n29448; p. 1(3); Jul. 21, 1994; Dialog: File 148, Acc#07478152.

Onsale Joins Fray as Online Shopping Picks Up Speed: Internet Booms; Computer Reseller News; Jun. 5, 1995; p. 73; Dialog: File 16, Acc#05649796.

Onsale Onsale Brings Thrill of Auctions and Bargain Hunting Online; Unique Internet retail service debuts with week-long charity auction for the Computer Museum in Boston, May 24, 1995; Dialog Abstract: File 610, Acc#0489267.

Pfeiffer, E. F., "The Glucose Sensor: The Missing Link in Diabetes Therapy", Hormone and Metabolic Research, (1990), vol. 24m Suppl. pp. 154-164.

Playmates Toys deals knockout blow to virtual pet competitors with introduction of Nano Fighter™ For Boys; New Nano Pet Fighting Pet Press Release; retrieved from URL http://www.virtualpet.com/vp/farm/nano/nfightpr.htm Apr. 23, 2000.

Playmates Toys leads Americas virtual pet craze into its next generation by introducting talking Nano Pals; Talking Nano Pet Press Release; Nov. 18, 1997; retrieved from URL http://www.virtualpet.com/vp/farm/nano/talkn/tnpress.htm on Apr. 23, 2000.

Poitout, V., et al. "A Glucose Monitoring System for On Line Estimation in Man of Blood Glucose Concentration Using a Miniaturized Glucose Sensor Implanted in the Subcutaneous Tissue and a Wearable Control Unit", Diabetologia, (1993), vol. 36, pp. 658-663.

Polson, Gary "Recent Developments and Trends in Keychain Virtual Pets," 1997 [retrieved on Apr. 23, 2000], Retrieved from <URL:www.virtualpet.com/vp/future/trends1a.htm>.

Potter, David, "Fundamentals of PC-Based Data Acquisition", Sensors, (Feb. 1994), pp. 12-20.

Reis, H, "Telemedicine: Transmitting Expertise to the Point of Care Toward an Electronic Patient Record"; '97, Nashville, TN, Apr. 27-May 3, 1997, pp. 248-256, v. 3.

Research project launched to improve health of America's communities; new Disney community in Florida is focus of program. Business Wire, p10011142. Oct. 1, 1996.

Results of the world's first on-line auction, http://www.christies.com. RO_AUCTION Auctioneers Property Database System and RO_AUCTION Auctioneers Accounting System; Ro-Auction features; Dec. 4, 1995.

Roberts; "Diabetes and Stress: A Type A Connection?", Psychology Today, (Jul. 1987), v. 21; pp22(1); Dialog: File 149, Acc# 05038381.

Rose, V. L., et al., "Decentralized Testing for Prothrombin Time and Activated Partial Thromboplastin Time Using a Dry Chemistry Portable Analyser", Archives of Pathology and Laboratory Medicine, (Jun. 1993), vol. 117, pp. 611-617.

Save the earth artrock auction, http://www.commerce.com.saveearth. Auction Web, http://www.ebay.com.

Schement, "An Intelligent Controller for Neurophysiological Experiments," Proceeding of the Annual Symposium on Computer Based Medical Systems, Durham, Jun. 14-17, 1992, p. 528, line 1-p. 529, line 21.

Schenkels, P., "Supplementary European Search Report", Application No. EP 97 92 2716, (Mar. 11, 2002).

Schork, Nicholas J., "Genetics of Complex Disease", Am.J.Respir. Crit. Care Me., (1997), vol. 156, pp. S103-S109.

Schrezenmeir, J. et al., "Computer Assisted Insulin Dosage Adjustment—Perspective for Diabetes Control", Hormone and Metabolic Research, Supplement Series, (1990), vol. 24, pp. 116-123.

Seigmann; "Nowhere to Go but Up"; PC Week; v12 n42, p. A5(1); Oct. 23, 1995; Dialog: File 148, Acc#08222496.

Seybold—New Horizons teams with Duke, Real Media; The Seybold Report on Desktop Publishing, v10 n12 p. 24(1), Aug. 12, 1996.

Shandle, Jack, "Who Will Dominate the Desktop in the 90's?", , Electronics, Feb. 1990, pp. 48-50. (3 pages) Cited by 2 patents.

Shults, Marc C., et al., "A Telemetry-Instrumentation System for Monitoring Multiple Subcutaneously Implanted Glucose Sensors", IEEE Transactions on Biomedical Engineering, (Oct. 1994), vol. 41, No. 10, pp. 937-942.

Skolnick et al. "Simultaneous Analysis of Multiple Polymorphic Loci Using Amplified Sequence Polymorphisms (ASPs)"; Genomics. 2: 273-279.

Soeldner, J. S., "Treatment of Diabetes Mellitus by Devices", The American Journal of Medicine, (Jan. 1981), vol. 70, 183-194.

Spitzer et al.; "The moderating effect of age on self-care"; Western Journal of Nursing Research, v18, n2, p136(13), Apr. 1996.

Talking Nano Puppy; retrieved from URL http://www.virtualpet.com/vp/farm/nano/talkn/talkn.htm Apr. 23, 2000.

Tamagotchi, 1997 [retrieved on Apr. 23, 2000], Retrieved from <URL:www.virtualpet.com/vp/farm/lleg/lleg.htm>.

Tandy Radio Shack , "The description of the Tandy Radio Shack TRS-80 Model 100/102 device available at http://www.old-computuers.com/musuem/computer.asp?c=233", World Wide Web, (Feb. 13, 2004), 1-3.

Telemedicine Provides Two-Way Computer Link for Parents of Very Premature Infants. PR Newswire. p1007NEM034. Oct. 7, 1996.

Theme Hospital, product review 1996 [retrieved Apr. 21, 2000], Retrieved from <URL:www.vigilante.co.uk/ep/misc/hospital.htm>.

Towards a partnership of care, M2 Presswire, Jun. 14, 2000.

United Healthcare's Optum Division goes online to better health by announcing a unique internet application. PR Newswire, p0801MNTH004. Aug. 1, 1996.

Updike, Stuart J., et al., "Laboratory Evaluation of New Reusable Blood Glucose Sensor", Diabetes Care, (Nov./Dec. 1998), vol. 11, No. 10, pp. 801-807.

Valla, et al., "A Structured Pictorial Questionnaire to Assess DSM-III-R-based Diagnosis in Children (6-11 years)"; Journal of Abnormal Child Psychology; v22 n4; p. 403(21); Aug. 1994; Dialog: File 88, Acc# 15759542.

Vallera, D. A., et al., "Accuracy of Portable Blood Glucose Monitoring", American Journal of Clinical Pathology, (1991), vol. 95, No. 2, pp. 247-252.

Virtual Pet Product Reviews, 1997 [retrieved on Apr. 23, 2000], Retrieved from <URL:www.virtualpet.com/vp/farm/reviews/reviews,htm>.

Virtual Tomagutchi, 1998 [retrieved Apr. 23, 2000], Retrieved from <URL:www.sttf.org/english/action/tomagutchi.html>.

Voelker, Rebecca, "Shoe Leather Therapy is Gaining on TB", Jama, (Mar. 13, 1996), vol. 275, 743.

Wilkins, Aaron. "Expanding Internet access for health care consumers", Health Care Management Review, Summer, Jul. 24-30, 1999.

Wyatt, J. C., "Clinical Data Systems, Part 2: Components and Techniques", Lancet, (Dec. 1994), vol. 344, No. 8937, pp. 1609-1614.

Yoshizawa, Daisuke, et al., "The Development of a Data Processing System with Personal Computer MSX Standard System for Flow Injection Analysis", Journal of Flow Injection Analysis, (1988), V.5, No. 2, pp. 101-110.

* cited by examiner

*Verification*

Update Existing Risk Model

DYNAMIC MODELING AND SCORING RISK ASSESSMENT

CROSS REFERENCE TO RELATED APPLICATIONS

The present application is a continuation of U.S. patent application Ser. No. 09/625,080 filed Jul. 25, 2000, now U.S. Pat. No. 7,305,348 which is a continuation of U.S. patent application Ser. No. 09/160,970 filed Sep. 25, 1998, issued as U.S. Pat. No. 6,240,393. Said U.S. patent application Ser. No. 09/625,080 and U.S. patent application Ser. No. 09/160,970 are hereby incorporated by reference in their entirety.

The following applications are hereby incorporated by reference:

U.S. patent application Ser. No. 09/159,219 filed Sep. 23, 1998 (abandoned)

U.S. patent application Ser. No. 09/159,058 filed Sep. 23, 1998 (abandoned)

FIELD OF THE INVENTION

The present invention relates generally to computer systems and more particularly to data structures for modeling and scoring risk assessment, such as insurance risk.

BACKGROUND OF THE INVENTION

In the insurance industry and in other fields in which risk is assessed (including such diverse fields as medical treatment, financial modeling and portfolio management, and environmental impact regulation), it is known to develop and use a risk-assessment model of a population. The risk-assessment model provides a technique for determining which population members are more subject or less subject to particular risks (or to an aggregate of risks) than the norm for that population. For example, in life insurance underwriting, it is known to evaluate past and present medical data so as to determine what insurance premium the underwriter wishes to charge.

While these known methods generally achieve the goal of assessing risk for particular individuals in comparison to a population norm, they have the drawback of making a risk assessment that is fixed at a particular point in time. That is, these risk-assessment models rely on static data, in particular (1) static data about the individual population member, (2) static data about the population norm, and (3) static data about risks associated or correlated with the data about the individual population member. However, risk for individual population members depends not only on their present data, but also on their future data, including both data about behavior and environment.

A first type of problem for the known art includes those individuals that have a progressive disease or degenerative condition, in which the disease or condition progresses at a rate that is responsive to behavior or environment of the individual. For such individuals, risk is more accurately evaluated as a function of behavior measured over time and environment measured over time, rather than as a static value that is a function only of present behavior and environment. For example, a first patient with diabetes can proceed with relatively small risk if that first patient is aware of and active in management of behavioral and environmental risk factors. In contrast, an otherwise identical second patient will have significantly greater risk if that second patient is either unaware of, or unable or unwilling to take charge of, behavioral and environmental risk factors.

Related to this first type of problem is the problem of determining trends for individual risk-assessment. For example, an individual with a history of diabetes may suffer a significant increase or decrease in effects thereof, due at least in part to that patient's actions with regard to behavioral and environmental risk factors. Similarly to the first type of problem, that individual will be rationally assessed a significantly greater or lesser risk than originally, if the new facts were known to the underwriter. Such trends may differ significantly from any trends that might have been discerned from past medical history alone; such trends may also themselves involve genetic, environmental, or behavioral components, or some combination thereof.

A second type of problem for the known art includes individuals whose risk-assessment significantly changes due to the vicissitudes of their life trajectory. This can include progression of a disease or condition, responsive at least in part to behavioral or environmental factors. For a more striking example, an individual may suffer a myocardial infarction, or become infected with an HIV variant. Similarly to the first type of problem, that individual would be rationally assessed a significantly greater risk than originally, if the new facts were known to the underwriter. Alternatively, an individual may be successfully treated for a "curable" disease such as Hodgkin's disease or some forms of cancer. Such vicissitudes of life trajectory may themselves involve genetic, environmental, or behavioral components, or some combination thereof.

A third type of problem for the known art includes individuals who significantly change their behavior or environment, particularly when those individuals are susceptible to the elements of their behavior or environment they change. For example, an individual with diabetes can determine to alter their diet favorably or unfavorably. For a more striking example, an individual may take up smoking or skydiving as habits. That individual will become a significantly greater risk than the underwriter originally assessed.

Moreover, new medical research may indicate risk factors that were not known at the time risk for the individual was originally assessed. These could include past medical information not known at the time to be important, tests available in the future for risk factors not known at the time at all, or changes in the medical history of the individual that place that individual in different risk factor categories. Such past medical information or risk factors may themselves involve genetic, environmental, or behavioral elements, or some combination thereof.

Accordingly, it would be advantageous to collect feedback from individual population members, whether on a periodic or aperiodic basis, and whether prompted by selected events or not. Such feedback would allow underwriters or other risk-assessment or risk-management personnel to determine specific risk-related information about each individual population member, and to adjust (such as to make more accurate or precise) insurance models and risk-assessment models to fit the new data. Such feedback enables the advantage of providing information about the time-varying nature of individual measures which can be used in the dynamic risk assessment model presented in the present invention. For instance, a weight gain of 10 pounds per year, an increase in diastolic blood pressure of 10 points per year, and an increase of cholesterol of 10 points per year could be tracked over time and would yield health risk information.

To achieve this advantage, a first aspect of the invention is that feedback is collected by a client-server system in which data is requested or required from population members. A server device, responsive to a risk-assessment model, prompts a client device supplied to population members to request information from population members, in order to determine whether aggregate measures or individual measures of risk-assessment remain in coherence with the model. The client device collects the data and supplies it to the server device, which can, in response to dynamically collected data, adjust the model, adjust risk assessments for selected population members (or groups thereof), or determine further information to collect from population members.

Upon achieving this advantage, a second aspect of the invention is to provide a set of superior risk-assessment models and insurance models in response to the feedback. These superior risk-assessment models and insurance models can include information about the risk-related behavior, risk-related trends, or forward-looking risk-assessment of selected individuals or selected subsets of the population. These superior risk-assessment models and insurance models can be responsive to data-mining techniques described in related patent applications, described below, hereby incorporated by reference as if fully set forth herein. These superior risk-assessment models can also incorporate known scientific information regarding health risk or disease progression, such as well-determined correlations of risk factors and disease incidence or progression from large research studies, or well-known shape of 5-year survival curves for patients having specific types of cancer.

Accordingly, it would also be advantageous to provide a set of techniques for modeling and scoring risk-assessment and a set of insurance products derived therefrom, using dynamic assessment of risk indicators and associated consequences for a population. This advantage is achieved in an embodiment of the invention in which a population (such as a population of medical patients) is assessed both at a selected time and afterward for those risk indicators and for consequences associated therewith. A client-server system provides dynamic data collection and analysis, dynamic risk assessment in response to that data collection and analysis, and dynamic treatment options and utilization review for each population member.

SUMMARY OF THE INVENTION

The invention provides a set of techniques for modeling and scoring risk-assessment and a set of insurance products derived therefrom. A set of risk indicators (such as medical risk factors for individuals) is determined at a selected time. A population (such as a population of medical patients) is assessed at the selected time and afterward for those risk indicators and for consequences associated therewith. For example, the population can be periodically assessed for correlation between smoking and heart disease, for correlation between alcohol use and heart disease, and for multivariate correlation of a plurality of such indicators and consequences.

In a preferred embodiment, selected population members are each coupled to client devices for determining risk indicators and consequences. For example, where the population is a set of medical patients, the client device can include a local device for asking medical, psychological and life-style questions, and for measurement of medical parameters, for each of those patients. A server device receives data from each client device, and in response thereto, can (1) reassess weights assigned to the risk indicators, (2) determine new significant risk indicators, (3) determine new significant measures for determining risk indicators and consequences, and (4) present treatment options to each population, member. The server device can perform these tasks in conjunction with an operator, such as a skilled medical professional, risk-management assessor, or other expert.

The server device can determine, in response to the data from each client device, and possibly in response to other data (such as provided by the expert operator), a measure of risk for each indicated consequence or for a set of such consequences. The server device can provide this measure with regard to each population member, or with regard to population subsets (selected either with regard to the known risk indicators or other indicators). The expert operator can use this measure to determine either (1) an individual course of treatment, (2) a resource utilization review model, (3) a risk-assessment model, or (4) an insurance pricing model, for each individual population member or for selected population subsets.

In a preferred embodiment, information requested by the client device, information determined and presented by the server device, and measurements determined in response thereto, can be adapted dynamically to changing aspects or changing membership of the population, or of an external environment having relevance to the population. For example, medical treatment or risk-assessment models can be dynamically adapted to an aging population or to biomedical advances with regard to detection or treatment of medical conditions for members of that population.

BRIEF DESCRIPTION OF THE DRAWINGS

FIG. 1b shows details of the client device 110 shown in FIG. 1a.

DESCRIPTION

In the following description, a preferred embodiment of the invention is described with regard to preferred process steps and data structures. Embodiments of the invention can be implemented using general purpose processors or special purpose processors operating under program control, or other circuits, adapted to particular process steps and data structures described herein. Implementation of the process steps and data structures described herein would not require-undue experimentation or further invention.

System for Data Collection

Figure 1A:
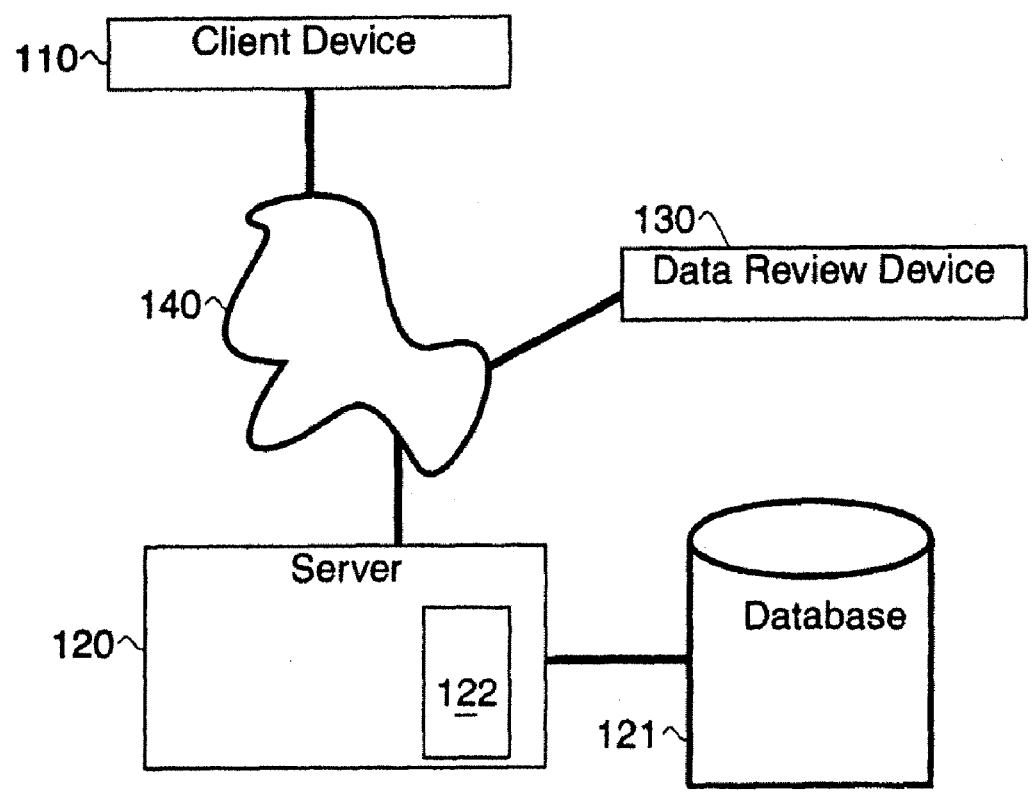
FIG. 1a shows a block diagram of a system for data collection and interpretation for a population.

FIG. 1a shows a block diagram of a system for data collection and interpretation for a population. Referring to FIG. 1a, a system 100 includes a client device 110, a server device 120 including a program memory 122 and database of patient information 121, and a data review element 130. These devices are connected via a communication channel, such as a communication network as in known in the art and more fully described in the Phenoscope and Phenobase patent (U.S. Ser. No. 09/041,809) and related patent application Ser. No. 08/946,341 and other patents and patent applications previously incorporated by reference.

Figure 1B:
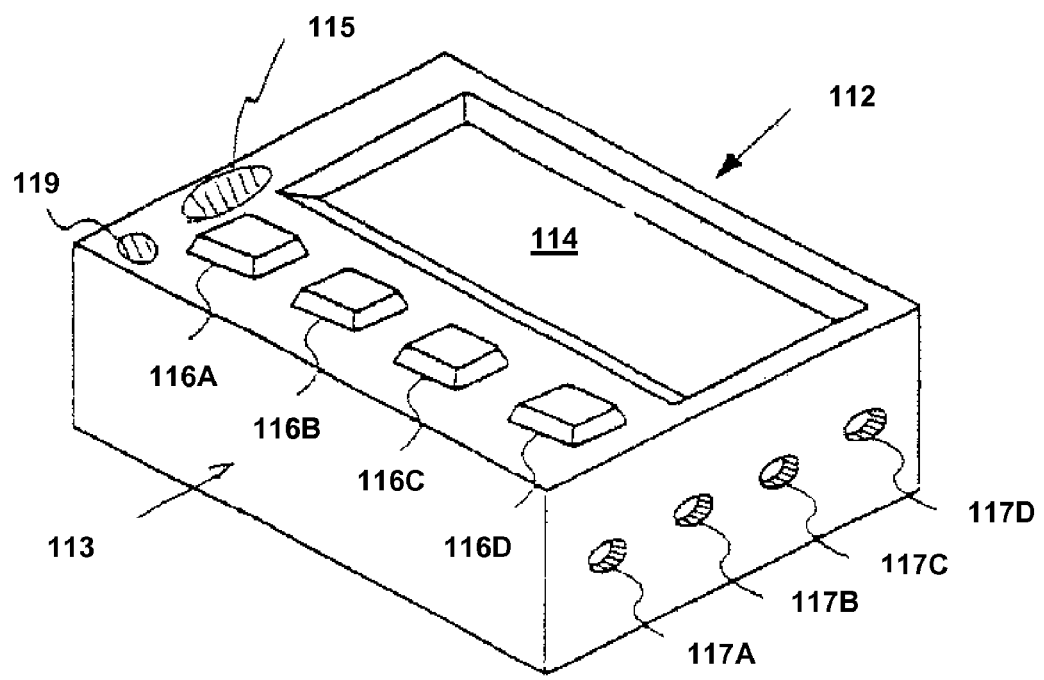

Referring to FIG. 1b, the client device 110 is disposed locally to a patient 111, and includes an output element 112 for presenting information to the patient 111, and an input element 113 for entering information from the patient 111. As used herein, "locally" refers to a logical relationship to the patient 111, and does not have any necessary implication with regard to actual physical position. In a preferred embodiment, the client device 110 is relatively small or compact, and can be disposed on a night table or otherwise near the patient 111.

The output element 112 includes a display screen 114, on which questions and suggested answers can be displayed for the patient 111, so as to facilitate information entry, or on which instructions can be displayed for the patient 111, so as to instruct the patient 111. The output element 112 can also include a speaker 115, so as to present information in conjunction with or in alternative to the display screen 114. The output element 112 can also include a bell or other sound element, or a bright light 119 or a flag, so as to alert the patient 111 that the client device 110 has questions or information for the patient 111.

The input element 113 includes a plurality of buttons 116A-D for entering information, preferably such as described in the patent applications referenced and incorporated by reference above.

Figure 1C:
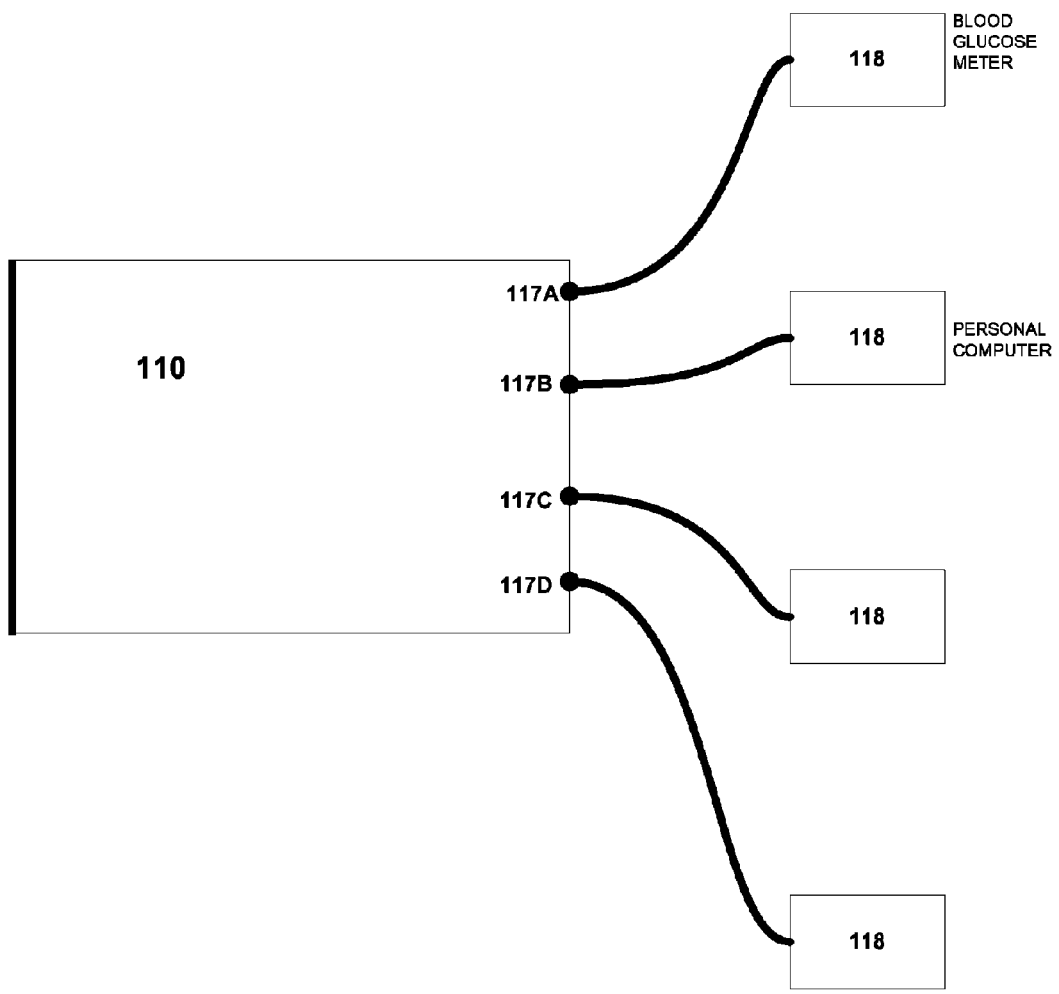
FIG. 1c shows devices that may be connected to client device 110.

The input element 113 can also include one or more data ports 117A-D for entering information from other devices. Referring to FIG. 1c, such other devices I 18 can include a medical measurement device, such as a blood glucose meter or a blood pressure monitor. Such other devices 118 can include a dispensing device for medication.

Such other devices 118 can also include a general purpose or special purpose client workstation, such as a personal computer or a hand-held digital calendar.

The server device 120 is disposed logically remotely from the patient 111, and includes a database 121 of information about the patient 111 and about other patients in a related population thereof. As used herein, "remotely" refers to a logical relationship to the patient 111, and does not have any necessary implication with regard to actual physical position.

The server 120 and patient profile database 121 are preferably accessible by means of a standard network connection such as a world wide web connection. Server 120 and database 121 may comprise single stand-alone computers or multiple computers distributed throughout a network.

Figure 1D:
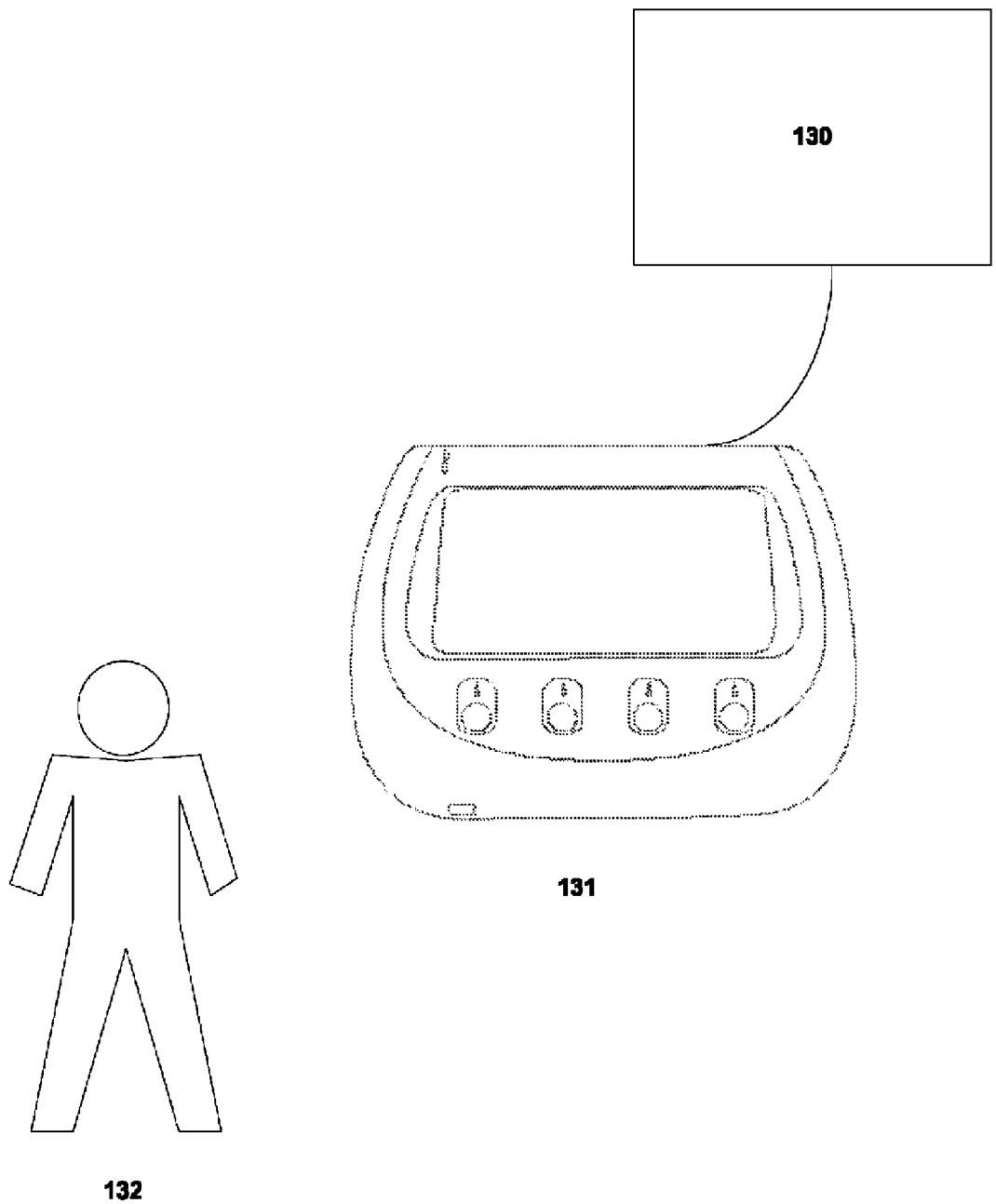
FIG. 1d shows details of the data review device.

Referring to FIG. 1a and FIG. 1d, the data review element 130 is disposed logically remotely from the patient 111, and includes an interface 131 disposed for use by an operator 132. The operator 132 can comprise medical personnel, a device operated by medical personnel, or a similar device, capable of interacting with the interface 131 so as to receive information from the data review element 130 and possibly to enter information into the data review element 130. Information entered into the data review element 130 can be entered for ultimate transmission to the server device 120 or to the client device 110.

The data review element 130 is preferably a personal computer, remote terminal, web TV unit, Palm Pilot unit, interactive voice response system, or any other communication technique. The data review element functions as a remote interlace for entering in server 120 or client device 110 messages and queries to be communicated to the individuals.

Aggregate Responses to Risk Indicators

Figure 2:
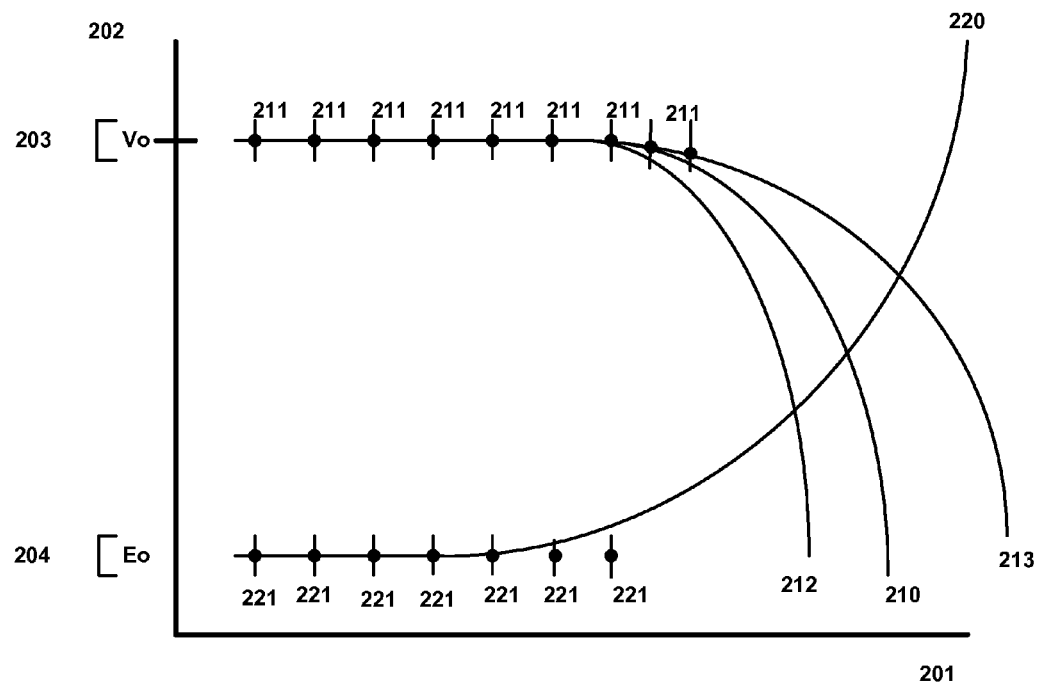
FIG. 2 shows a response diagram of consequences to risk indicators, for statistical aggregates of the population, which can be selected in response to dynamic data collection and analysis.

FIG. 2 shows a response diagram 200a of consequences to risk indicators, for statistical aggregates of the population, which can be selected in response to dynamic data collection and analysis. It is to be noted that FIG. 2 shows curves that are collapsed to 2-dimensions, in a preferred embodiment the curves are N-dimensional, with N>2.

A diagram 200a includes a first axis X 201 and a second axis Y 202. The diagram shows a first response curve RO 210 showing a normal trajectory for vital function and life expectancy of an individual or subpopulation of the population. The first axis X 201 indicates a relative time, as measured toward a right side of the diagram. The scale of the first axis X 201 is a relative time whose initial left hand point may be undetermined. As to a first response curve RO 210, the second axis Y 202 represents a measure of vital function and life expectancy.

A diagram 200a also shows a second response curve SO 220 showing a normal trajectory for a measure of expected medical expense or risk for an individual or subpopulation of the population. The first axis X 201 indicates a relative time as for a first response curve RO 210. As to a second response curve SO 220, the second axis Y 202 shows increasing expense or risk as measured toward the top of the diagram.

In the first response curve RO 210, the normal trajectory for vital function and life expectancy for a typical individual in the population shows that as time progresses, vitality and life expectancy are expected to decrease. This general concept is known in the art of actuaries. It is to be noted that the shape shown by the first response curve RO 210 is an example shape; for instance, it is known that for certain curable cancers, risk increases, then levels off after a certain length of time such as a 5-year survival rate, then later in life risk increases due to other causes.

The first response curve RO 210 includes a number of points with error bars 211 about the response curve RO 210. All of the points 211 are at an identical value, VO, of the second axis Y 202, with identical error bars. Any one of the points represents a single measurement of vitality taken for an individual. Given any single measurement of vitality, it is difficult to determine where along the second axis X 201, that is, where along the trajectory the individual is. Of particular interest is how close to a rapid decline in vitality or increase in risk the individual is. The points 211 show the several places along the curve where the individual might be placed, based on this single measurement of vitality. Because the response curve RO 210 is slowly varying through much of the time, that is, the values of vitality and life expectancy clustering in a selected region of the second axis Y 202, shown by the bracket 203, and due to margins of error in both the measurement as well as the response curve, there are several positions along the curve where an individual with a specific measurement might be; these several positions are shown by points 211.

By contrast, if measurements are taken for an individual at more than one point in time, greater information is present, and in particular trends may be discerned which yield more information about where on the curve an individual is. This ability to discern trends is greater when curves in N-dimensions are considered. For instance, an individual whose excess weight has slowly climbed in conjunction with slowly increasing cholesterol, blood pressure, stress levels and family medical history would be placed in a greater risk category although the individual measures of, for instance, cholesterol, might be within a normal range.

Similarly, in the second response curve SO 220, the normal trajectory for expected medical expense and risk for that typical individual shows that as time progresses, expected medical expense and risk are expected to increase. This general concept is also known in the art of actuaries. It is to be noted that the shape shown by the second response curve RO 220 is an example shape; for instance, upon diagnosis of a disease the expense may climb, but if the patient is cured the expense will level off.

Similarly, the second response curve SO 220 includes a number of points 221 on the response curve SO 220, showing possible places that an individual in the population with measurement of expense or risk, with value E0, might be. Because most of the values of response curve SO 220 cluster in a selected region of the second axis Y 202 shown by the bracket 204, it is difficult to know where along curve SO 220 an individual with measurement E0 should be placed. This is due to both possible error in measurement of E0 as well as uncertainty in the exact "true" position and shape of curve SO 220. As for curve RO 210, measurements of expense or risk taken over time will yield useful information about where on the curve SO 220 an individual is.

Figure 5:
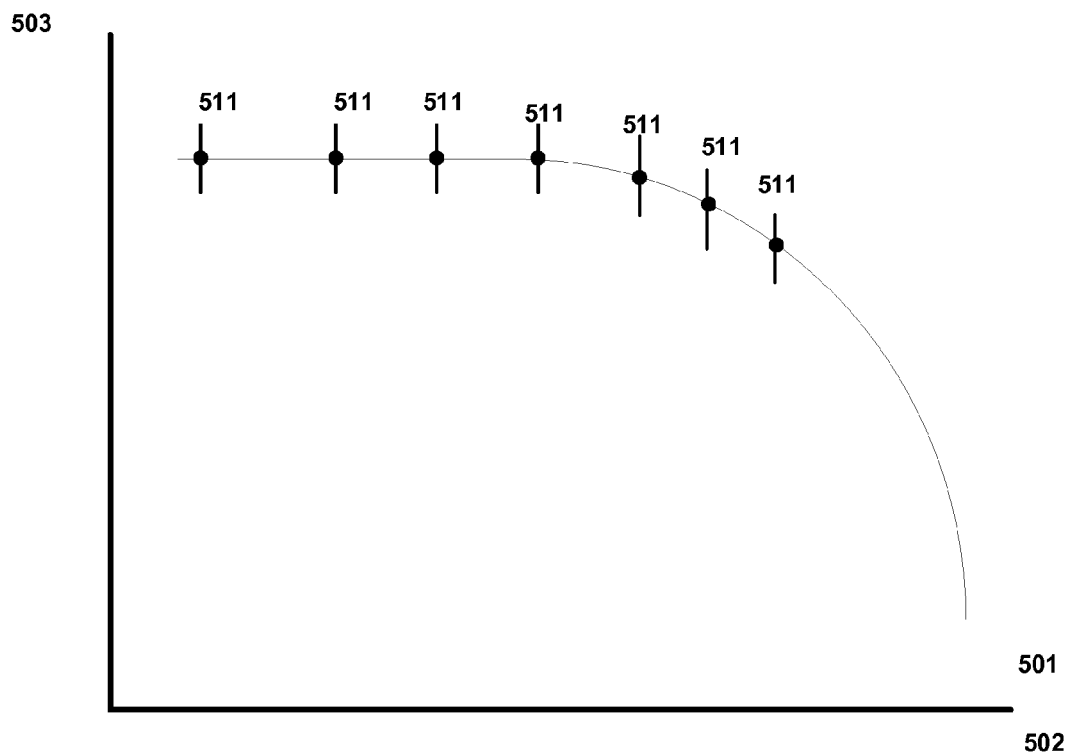
FIG. 5 shows a response diagram of consequences to risk indicators, for statistical aggregates of the population, with data collected from an individual at different points of time also plotted.

When subsets of the population are selected in response to specific risk factors, the statistical aggregates of the population can differ substantially from the aggregate response curves RO 210 and SO 220 for the entire population. The diagram 200a shows response curves R1a 212 and R1b 213 showing a normal life trajectory for vital function and life expectancy of an "average" individual in the population, depending on whether that individual is associated with a selected risk factor a. As with regard to the aggregate for the entire population, it is difficult to determine from a specific single measurement just where on either response curve R1a 212 or R1b 213 the individual should be assessed. Depending on whether the value of a is known for an individual, it may also be difficult to know whether the individual should be placed on response curve R1a 212 or R1b 213. Measurements of several risk indicators taken over time may yield information on whether a specific individual should be placed in category R1a 213 or the higher risk category R1b 212. The general concept of using time-dependent information to determine risk along is also illustrated in FIG. 5.

The client device 110 determines information from which the server device 120 or the data review element 130 can analyze the time varying nature of data. The server device 120 or the data review element 130 can therefore determine both of the following: (1) just where on either response curve R1 a 212 or R1b 213 the individual should be assessed; and (2) whether the individual should be assessed on the response curve R1a 212 or the response curve R1b 213.

It is to be noted that the above analysis has been condensed to 2-dimensions for convenience in presentation, with a single measurement along a single X-axis or Y-axis. In a preferred embodiment, a measurement would have many attributes, i.e. the model would have N-dimensions, and more sophisticated techniques for analyzing trends and achieving objectives are used.

If the data for the population is not known for all individuals in the population or subpopulation of interest, the server device 120 transmits a new set of information-gathering instructions (such as questions and suggested answers) to the client device 110, so as to measure that information individually for each patient 111.

Dynamic Modeling and Risk Evaluation

Figure 3A:
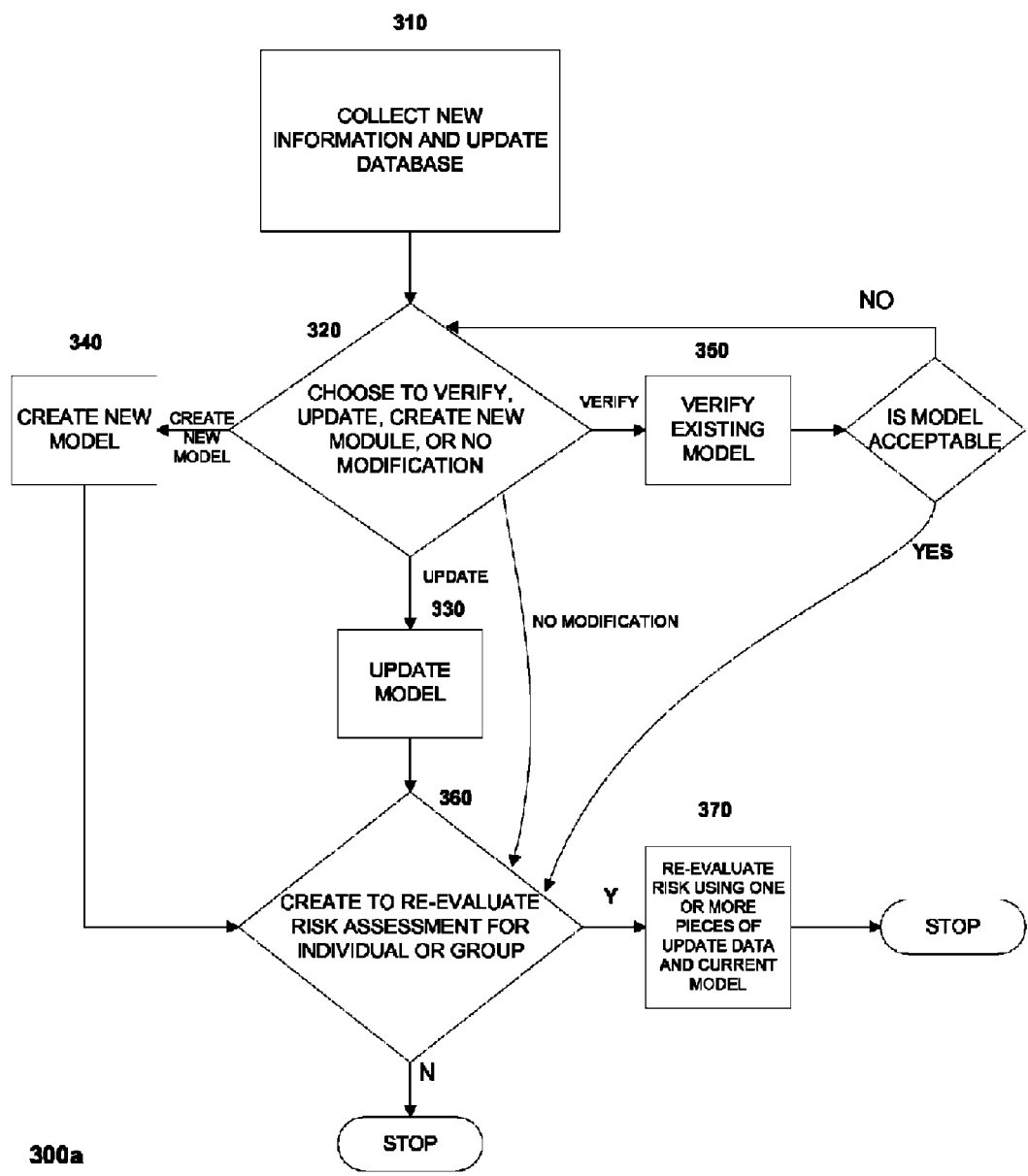
FIG. 3a shows a process flow diagram of a method for dynamic data collection to be performed by the system; verification of model, updating a model, or creating a new model, and re-evaluation of risk assessment.

FIG. 3a shows a process flow diagram 300a for a method with steps of dynamically collecting information 310, choosing to verify or update the model or to create new model 320, verifying 350 or updating 330 the risk assessment model or creating a new model 340, deciding whether to re-evaluate risk 360 and re-evaluating risk based on updated information and current model 370.

Dynamic Data Collection for Population

Figure 3B:
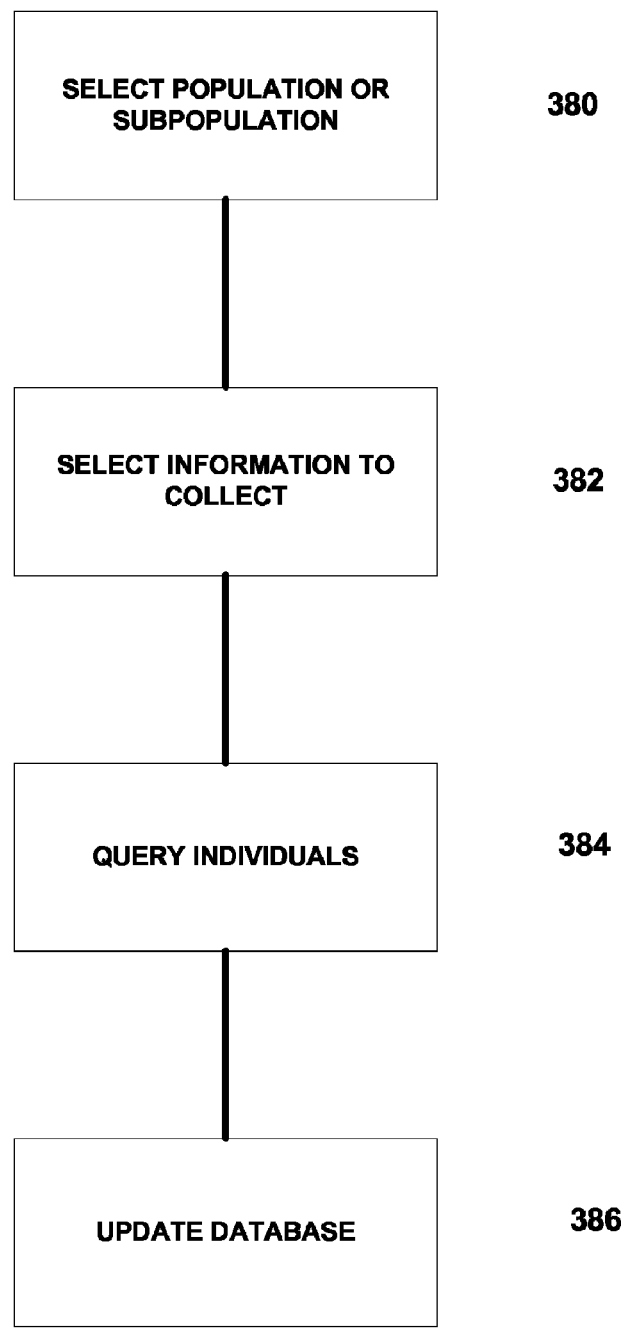
FIG. 3b shows a process flow diagram of the step of dynamic data collection.

FIG. 3b shows a process flow diagram 300b of a method for dynamic data collection to be performed by the system. This data collection may be done periodically or aperiodically, upon a triggering event or decision by the expert operator. The population or subpopulation from which to collect data is selected 380. The selection criteria may be based on preset values or may be set by the expert operator. The set of risk indicators or other information to be collected is selected 382, based either on preset values or decision by the expert operator. The individuals in the subpopulation of interest are queried 384 as to the information of interest and the database is updated 386. "The pre-query steps need not be done in the order indicated.

Verification of Existing Model and Update of Model

Figure 3C:
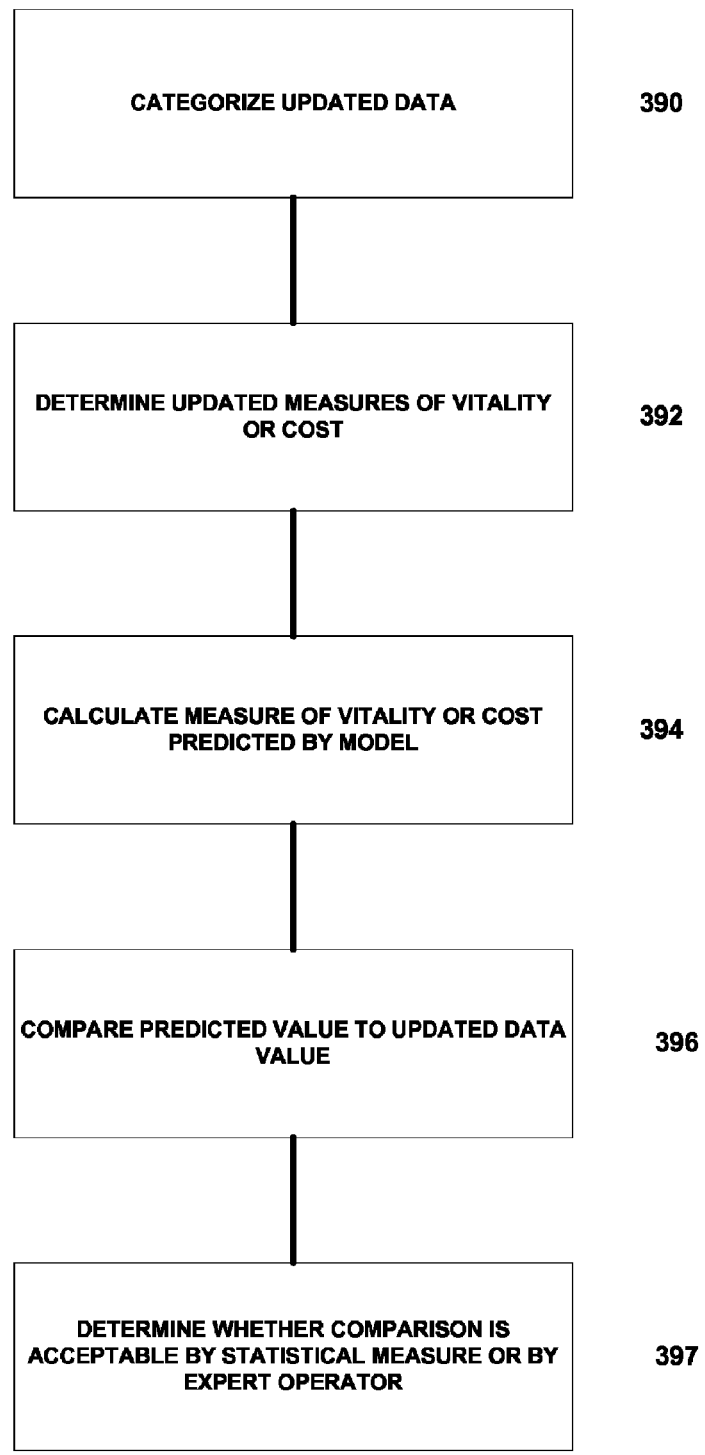
FIG. 3c shows a process flow diagram of the step of verification of the model.

FIG. 3c shows a process flow diagram 300c of a method by which the updated data can be analyzed to determine whether the existing model is consistent with the updated data; that is, to verify that the data conforms to the model within acceptable variation or error. This is accomplished by putting the updated data into categories 390, determining the updating measures of life vitality or costs 392, determining the values predicted by the model 394, comparing the updated measures of life vitality or costs against those predicted by the model 396. and determining whether the comparison is acceptable 397. If the predicted value is within an acceptable distance from the updated values based on well known measures such as statistical error, then the model need not be adjusted. The expert operator may also visually determine whether the updated data and existing model show an acceptable relationship to each other.

Figure 3D:
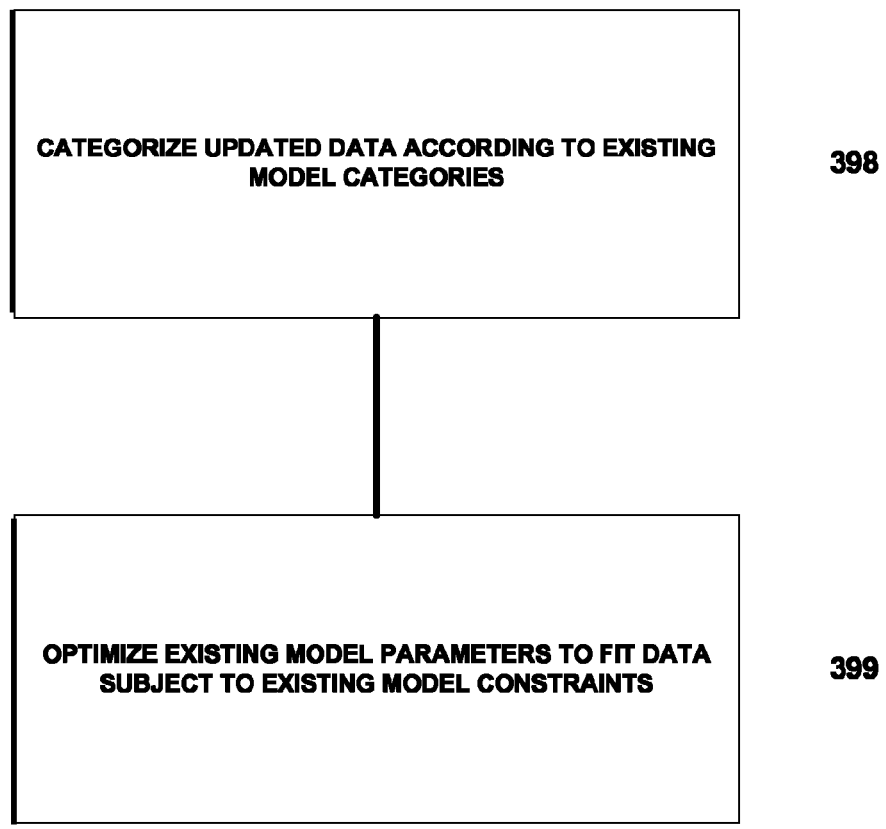
FIG. 3d shows a process flow diagram of the step of updating the existing model.

FIG. 3d shows a process flow diagram 300d of a method for updating the existing risk model in response to updated information. By updating, it is meant that no new risk indicators are added, and no new external constraints on the model are added. The risk model to be adjusted may be for the aggregate population or for various subpopulations. The updated information for the subpopulation is categorized 398 according to profile information into one or more existing categories. The subpopulation is categorized according to one or more existing measure of life vitality or medical expense. Statistical analyses as described below or in other patents or patent applications previously incorporated by reference or as known in the art of statistics are applied to determine updated values for model parameters such as weights to give each factor 399

Re-Evaluating Risk Assessment Based on Updated Information

As shown in FIG. 3a, a current model can be determined based on updated information. Once a current model is determined, which may include simply using the already existing model, individual or subpopulation risk assessment may be reevaluated in response to one or more pieces of updated information, as desired by the expert operator or as a preprogrammed operation.

Dynamic Data Analysis for Population

Figure 4A:
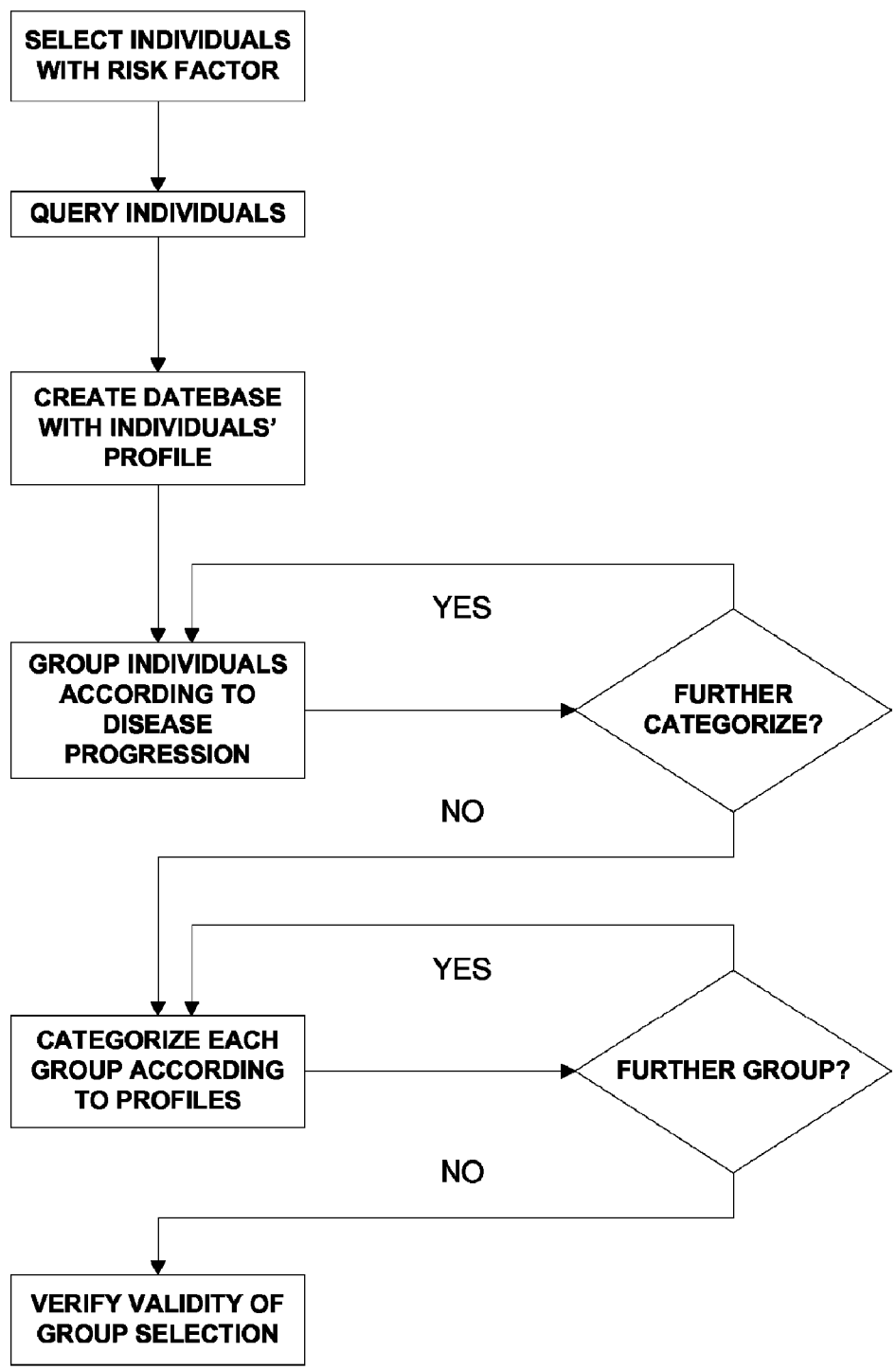
FIG. 4a shows a process flow diagram of a method for dynamic data analysis to be performed by the system.

FIG. 4a shows a process flow diagram 400a of a method for dynamic data analysis ("data mining") to be performed by the system. The updated database can be mined to create a new model that may include reassessment of weights assigned to the risk indicators, addition of new significant risk indicators, or determination of new significant measures for determining risk indicators and consequences. Applied examples of data mining and additional explanation are shown in the related application Ser. No. 09/041,809 and other applications referenced above.

Figure 4B:
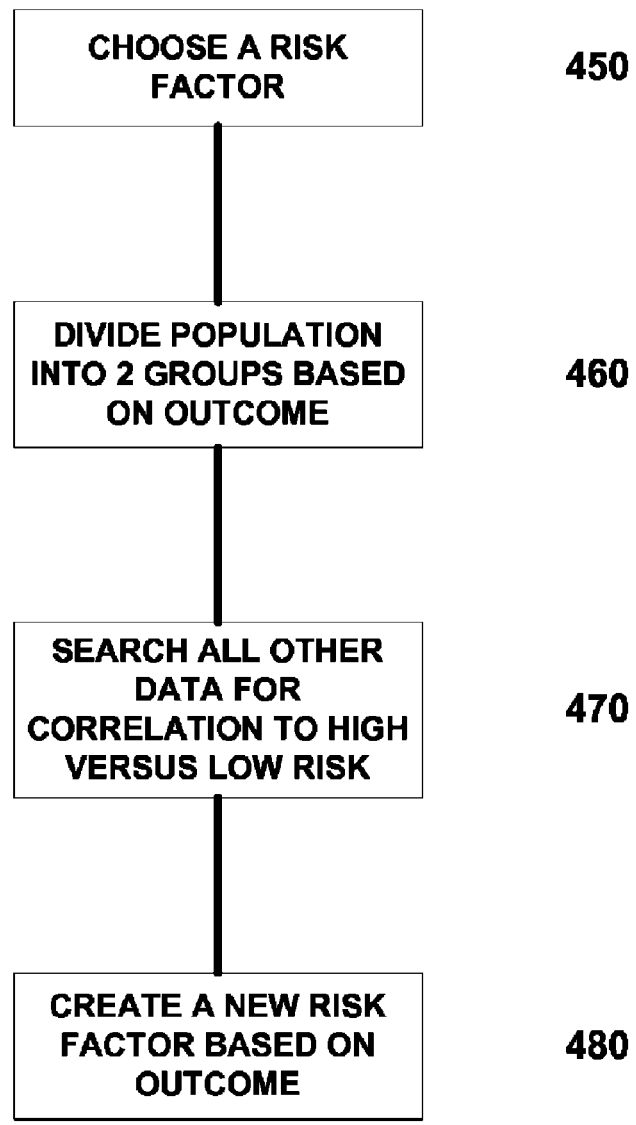
FIG. 4b shows a process flow diagram for data mining.

FIG. 4b shows a process flow diagram of a method of using the statistical method of calculating correlations on subpopulations, following the steps of: (1) choose a risk factor 450; (2) divide the risk pool into two groups based on outcome 460; (3) search all other data for correlation to high versus low risk 470; (3) create a new risk factor based on this correlation 480. The new risk factor may be a discrete piece of data that was asked of the client but was not previously known to be a significant predictor, or it may be a new factor that is generated by combining other pieces of data. FIG. 4b is a process flow diagram of the above steps.

In addition to data mined from the database, in creating a new model, scientific information well known in the literature may supplement the data. For instance, scientific information regarding certain well studied correlations be considered such as known correlations of time since quitting smoking and various health conditions, known information regarding the shape of life expectancy curves for certain types of cancer patients, or recent information regarding efficacy of new forms of treatment for diseases such as recent significant improvements in treatment of AIDS.

Statistical analyses are known in the art of statistics, and include correlation analyses, multivariate regressions, constrained multivariate regressions, or variance analyses, may also be run on the data to reveal statistical relationships among the various information or measures of life vitality or medical expense in order to improve the predictive power of a model, although in a preferred embodiment data mining is done as presented in the preceding paragraphs.

Modeling and Scoring Risk Assessment, Insurance Pricing

Modeling risk is performed by assigning risk to individual in response to risk factors identified for that individual, and such modeling may be done for the population or for a subpopulation. There are many techniques for modeling, such as linearly risk scoring by assigning a number to each risk factor and adding up each number to determine a total risk score, non-linearly assessing risk by combining risk factors non-linearly to determine risk which may be achieved by neural network techniques which are known in the art of neural networks, or other techniques.

FIG. 5 shows a diagram 500 including a first axis X 502 and a second axis Y 503 and a response curve RO 501, similar to that shown in FIG. 2. It shows several measurements of vitality with error bars 511 of an individual taken at several different points in time. Each measurement of vitality is taken at a later time from left to right. Information about the time varying nature of the measurements, or the trends, can improve the ability to predict future vitality, including imminent sharp declines in vitality, as can been seen by visually examining the data over time or by using sophisticated statistical techniques to examine the data and trends in the data over N-dimensions.

Insurance pricing may be achieved from advantages in risk assessment. It is known in the art of actuarial analysis to assign price in response to risk.

Providing Treatment Options and Information to each Population Member

Figure 6:
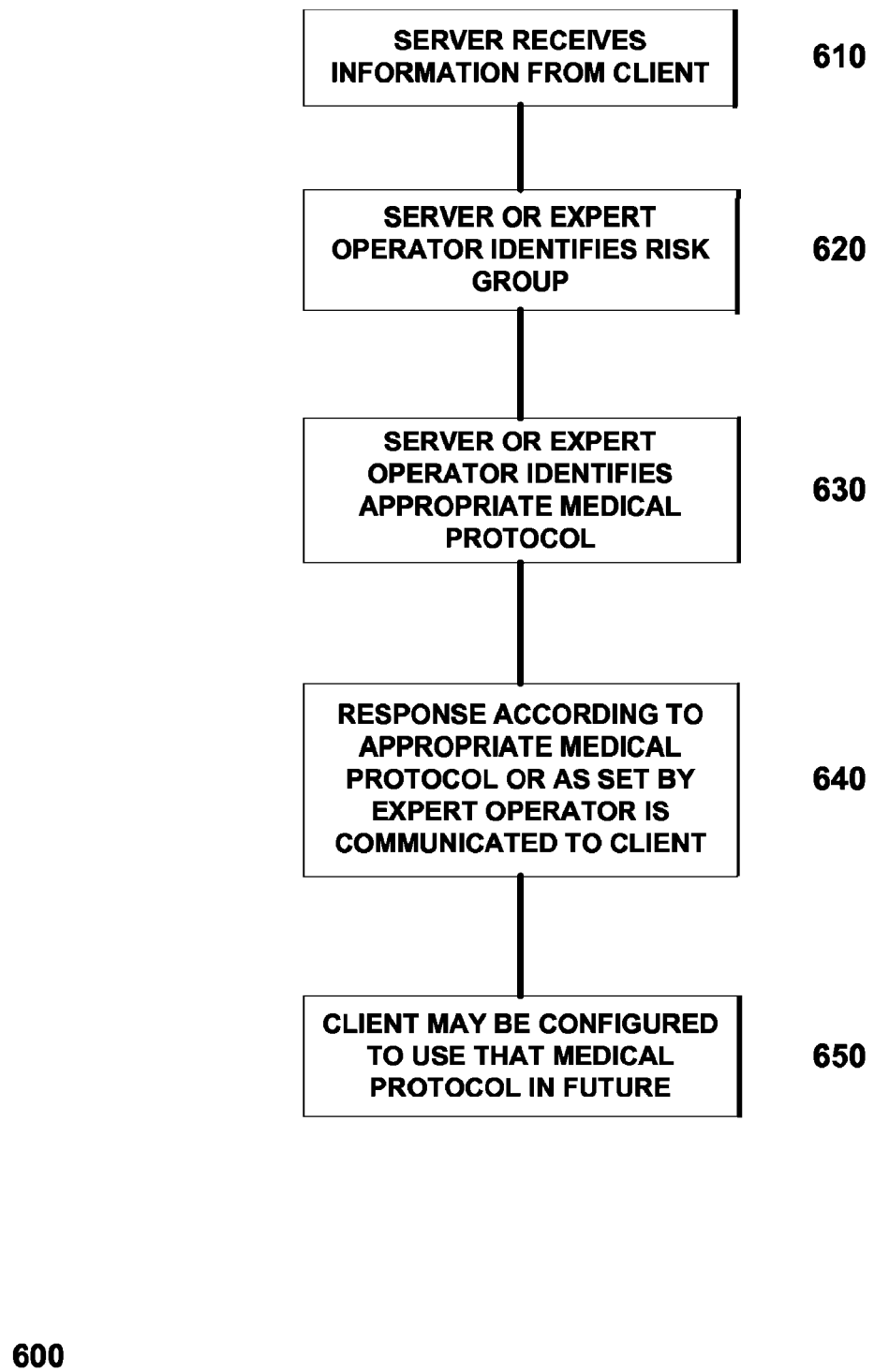
FIG. 6 shows a process flow diagram for a method of providing treatment options and information to each patient based on the data provided to the server.

FIG. 6 is a process flow diagram 600 showing a method for providing treatment options and information to each member based on the information provided. Upon receiving information about the patient from the client 610, the server or expert operator may identify a risk group 620 and identify an appropriate medical protocol 630, the server may present one or more responses to the patient 640, including treatment options, advice or merely health information that would be useful to the patient, and the client device may be configured to use an appropriate medical protocol in interacting with the patient 650. It is known in the art of medicine that membership in a risk group may indicate appropriate treatment. This may be done from an automated, preset set of responses to individual queries made to the patient, on an aggregate of preset responses to queries, or by an expert operator.

ALTERNATIVE EMBODIMENTS

Although preferred embodiments are disclosed herein, many variations are possible which remain within the concept, scope, and spirit of the invention, and these variations would become clear to those skilled in the art after perusal of this application.

What is claimed is:

1. A system for determining compliance with a regimen, comprising:
    a client device associated with each individual of a group, the client device configured for acquiring a first set of data from each individual of the group and a second set of data from each individual of the group, said client device including a display, an input device for receiving information, an output device configured to alert an individual that information is requested from the individual and a data port, the second set of data being acquired after a time period has elapsed after acquisition of the first set of data;
    a medical measurement device coupled to said data port of said client device, the medical measurement device configured for obtaining measurement data from each individual of the group, the medical measurement device including at least one of a blood glucose meter, blood pressure monitor and medication dispensing device, the client device configured for receiving the measurement data and for integrating said measurement data within said first set of data and said second set of data; and
    a server device, the server device operably connected to the client device associated with each individual of a group via a communication pathway, the server device configured for analyzing the first set of data and the second set of data to assess a change for the group by comparing the second set of data to the first set of data after performing a regimen, said regimen including a prescribed diet, exercise and medication, wherein an award is distributed to the group based upon the change.

2. The system as claimed in claim 1, wherein the client device prompts each individual of the group to enter the first set of data and the second set of data into the client device.

3. The system as claimed in claim 1, wherein the communication pathway is established between the client device and the server device by at least one of an internet connection, an intranet connection, a local area network, a telephone connection, a wireless connection, a cable connection, a satellite connection, a router connection, an Ethernet connection, a serial connection, a USB connection, a firewire connection, a microwave connection and a cellular connection.

4. The system as claimed in claim 1, wherein the award is distributed to the group for improvement in a measure of a health condition.

5. The system as claimed in claim 1, wherein the award is at least one of a reduction in an insurance premium, a pecuniary benefit, an expansion of insurance coverage, a bonus, an incentive, and a continuance of insurance coverage.

6. The system as claimed in claim 1, wherein said output device of said client device includes an audio element and video element.

7. The system as claimed in claim 1, wherein said audio element is a speaker.

8. The system as claimed in claim 1, wherein said output device of said client device is configured to alert said individual that information is requested from the individual according to a periodic schedule.

9. The system as claimed in claim 1, wherein said output device of said client device is configured to alert said individual that information is requested from the individual according to an aperiodic schedule.

10. The system as claimed in claim 1, wherein said output device of said client device is configured to alert said individual that information is requested from the individual after a triggering event.

* * * * *